United States Patent
Hah et al.

(10) Patent No.: US 10,174,047 B2
(45) Date of Patent: Jan. 8, 2019

(54) THIENODIAZEPINE DERIVATIVES OR PHARMACEUTICALLY ACCEPTABLE SALTS THEREOF, AND PHARMACEUTICAL COMPOSITION INCLUDING THE SAME AS AN ACTIVE INGREDIENT

(71) Applicant: Industry-University Cooperation Foundation Hanyang University ERICA Campus, Ansan-si (KR)

(72) Inventors: Jung-Mi Hah, Seoul (KR); Jung Hun Lee, Suwon-si (KR); Minjung Kim, Seoul (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 0 days.

(21) Appl. No.: 15/551,926

(22) PCT Filed: Jul. 13, 2015

(86) PCT No.: PCT/KR2015/007257
§ 371 (c)(1),
(2) Date: Aug. 18, 2017

(87) PCT Pub. No.: WO2016/137060
PCT Pub. Date: Sep. 1, 2016

(65) Prior Publication Data
US 2018/0037589 A1   Feb. 8, 2018

(30) Foreign Application Priority Data
Feb. 23, 2015   (KR) .................. 10-2015-0025384

(51) Int. Cl.
| | | |
|---|---|---|
| C07D 495/04 | (2006.01) | |
| A61K 31/5517 | (2006.01) | |
| A61K 31/551 | (2006.01) | |
| C07D 243/00 | (2006.01) | |
| C07D 333/00 | (2006.01) | |

(52) U.S. Cl.
CPC .......... C07D 495/04 (2013.01); A61K 31/551 (2013.01); A61K 31/5517 (2013.01); C07D 243/00 (2013.01); C07D 333/00 (2013.01); *A61K 2300/00* (2013.01)

(58) Field of Classification Search
CPC ................................................ C07D 495/04
See application file for complete search history.

(56) References Cited

U.S. PATENT DOCUMENTS

| | | |
|---|---|---|
| 3,669,959 A | 6/1972 | Hromatka et al. |
| 3,872,089 A | 3/1975 | Hromatka et al. |
| 3,887,543 A | 6/1975 | Nakanishi |
| 3,965,111 A | 6/1976 | Nakanishi et al. |
| 4,900,729 A | 2/1990 | Stransky |
| 5,492,906 A | 2/1996 | Braquet |
| 5,602,125 A | 2/1997 | Carling et al. |
| 5,712,274 A | 1/1998 | Sueoka et al. |
| 2014/0018353 A1 | 1/2014 | Bertoni et al. |

FOREIGN PATENT DOCUMENTS

| | | |
|---|---|---|
| EP | 0661284 | 7/1995 |
| KR | 10-1992-0003981 | 5/1992 |
| KR | 10-1995-7003566 | 9/1995 |
| KR | 10-1997-0002640 | 3/1997 |

OTHER PUBLICATIONS

PCT Search Report & Written Opinion, Patent Cooperation Treaty, dated Jun. 9, 2016, Application No. PCT/KR2015/007257.
Manning et al., "The Protein Kinase Complement of the Human Genome", Science, 298, 1912 (2002).
Avruch, J. et al., "Ras Activation of the Raf Kinase: Tyrosine Kinase Recruitment of the MAP Kinase Cascade", Recent Progress in Hormone Research, 2001, 56, 127.
Nancy H. Tran et al., "B-Raf and Raf-1 Are Regulated by Distinct Autoregulatory Mechanisms", The Journal of Biological Chemistry, 2005, vol. 280, pp. 16244; Wellbrock, C. Nature Reviews Molecular Cell Biology, 2004, 5, 875.
Jaiswal, R.K. et al., "Nerve Growth Factor-mediated Activation of the Mitogen-activated Protein (MAP) Kinase Cascade Involves a Signaling Complex Containing B-Raf and HSP90", The Journal of Biological Chemistry, 1996, vol. 271, pp. 23626.
Chimirri, A., et al. "Structure-Activity Relationships in Thienodiazepine and Benzodiazepine Derivatives",Farmaco., 1994, 49(3), 193-196.
Chimirri, A., et al. Thieno(3,4-b)(1,4)diazepines: Synthesis and Stereochemistry, Heterocycles. 1992, 34(6), 1191-1200.

*Primary Examiner* — Bruck Kifle
(74) *Attorney, Agent, or Firm* — Lex IP Meister, PLLC

(57) ABSTRACT

The present invention relates to novel thienodiazepine derivatives or pharmaceutically acceptable salts thereof, and a pharmaceutical composition including the same. The thienodiazepine derivatives or pharmaceutically acceptable salts thereof exhibit selective inhibition activities against protein kinases such as c-Kit, FLT3, FMS, LYN, RAF1, VEGFR3, PDGFRa, PDGFRb, RET, etc., and thus can be used as a pharmaceutical composition for prevention or treatment of abnormal cell growth diseases.

3 Claims, 1 Drawing Sheet

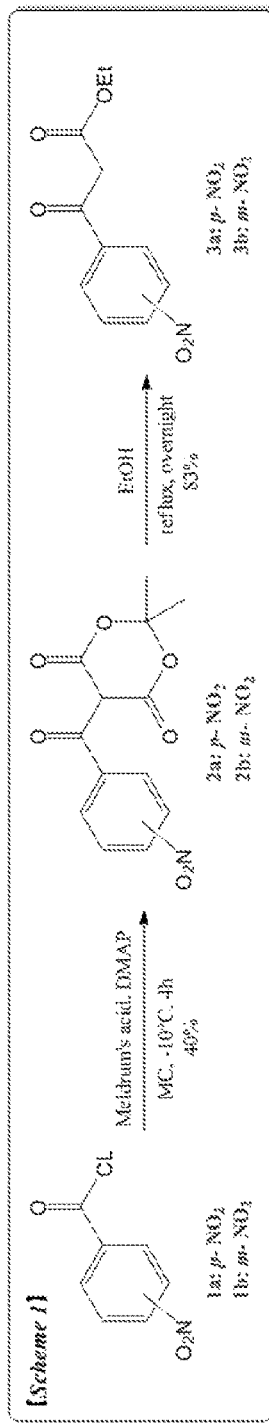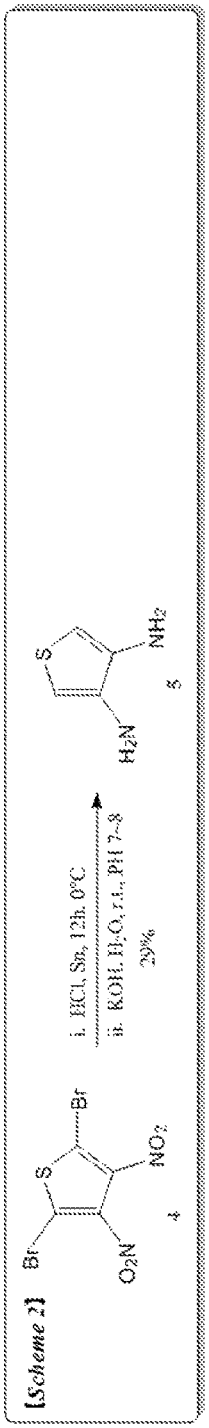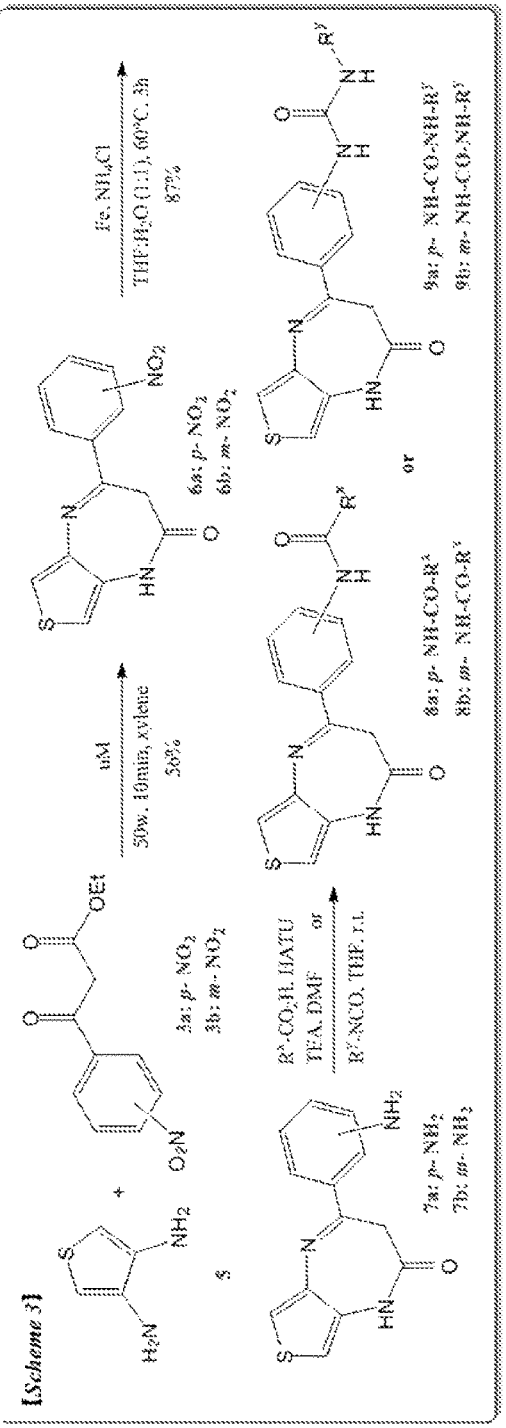

THIENODIAZEPINE DERIVATIVES OR PHARMACEUTICALLY ACCEPTABLE SALTS THEREOF, AND PHARMACEUTICAL COMPOSITION INCLUDING THE SAME AS AN ACTIVE INGREDIENT

CROSS-REFERENCE TO RELATED APPLICATION(S)

This application claims the benefit of priority from Korean Patent Application No. 10-2015-0025384 filed on Feb. 23, 2015 with the Korean Intellectual Property Office, the disclosure of which is incorporated herein by reference in its entirety.

TECHNICAL FIELD

The present invention relates to thienodiazepine derivatives or pharmaceutically acceptable salts thereof, and a pharmaceutical composition including the same as an active ingredient.

BACKGROUND OF ART

Despite tremendous advances in cancer research over many years, cancer is still the second leading cause of death worldwide. For cancer treatment, extensive studies on the mechanisms thereof have revealed many specific molecular targets. Practically, cancer-targeted therapies have been very successful, particularly in the case of kinase inhibitors. Protein kinases are enzymes that catalyze the phosphorylation of hydroxy groups located in tyrosine, serine, and threonine residues of proteins, and play an important role in signal transduction of growth factors inducing cell growth, differentiation, and proliferation.

A signal transduction pathway should maintain a good balance between turning on and off so as to maintain homeostasis. However, mutations or overexpression of specific protein kinases disrupt the signal transduction pathway in normal cells (mainly, conditions wherein signal transduction in the body is continued), thus inducing various diseases such as cancer, inflammation, metabolic diseases, brain diseases, etc.

It is assumed that 518 kinds of human protein kinases exist, which correspond to about 1.7% of all human genes (Manning et al, Science, 2002, 298, 1912), and they are largely divided into tyrosine protein kinases (90 or more kinds) and serine/threonine protein kinases. Tyrosine protein kinases may be divided into 58 kinds of receptor tyrosine kinases that are classified into 20 subfamilies, and 32 kinds of cytoplasmic/non-receptor tyrosine kinases classified into 10 subfamilies. The receptor tyrosine kinases have a domain capable of accepting growth factors on the cell surface, and an active region capable of phosphorylating tyrosine residue in the cytoplasm. If a growth factor is bound to the growth factor receptor site on the cell surface of the receptor tyrosine kinase, the receptor tyrosine kinase forms a polymer and the tyrosine residue of cytoplasm is self-phosphorylated. Further, through sequential phosphorylation of the lower series of proteins, signal transduction is progressed into the nucleus, and ultimately, transcription factors inducing cancer are overexpressed.

Raf is serine/threonine (Ser/Thr) protein kinase, and plays a role for transducing signals sent by growth factor receptors activated in the cell membrane into the nucleus. A mitogen-activated protein kinase (MAPK) signal transduction pathway is essential for cell proliferation/differentiation/survival/apoptosis, etc., and is formed by the sequential phosphorylation of largely three kinases {MAPK kinase kinase (MAPKKK), MAPK kinase (MAPKK), and MAPK}. Raf is a MAPK kinase kinase (MAPKKK), MEK is a MAPK kinase (MAPKK), and extracellular signal-regulated kinase (ERK) is a MAPK. If a receptor is activated, a small GTP-binding protein Ras is activated, and through the sequential phosphorylation of Raf-MEK-ERK, MAPK signal transduction into the nucleus is achieved.

Meanwhile, a Ras oncogene that always maintains an activated state (particularly, k-Ras) is closely related to the induction of solid cancer such as pancreatic cancer (about 90%), rectal cancer (about 45%), liver cancer (about 30%), non-small cell lung cancer (about 35%), kidney cancer (about 10%), etc. If Raf-1 binds with activated Ras and the 338th serine of Raf-1 is phosphorylated (Avruch, J., Recent Progress in Hormone Research, 2001, 56, 127), Raf-1 is activated. To the contrary, if the 14-3-3 protein binds to Raf-1 of which 259th serine is phosphorylated, Raf-1 is inactivated.

The three subclasses of Raf protein (A-Raf, B-Raf, and C-Raf/Raf-1) have three conserved regions (CR1, CR2, and CR3) in the N-terminal control domain and C-terminal kinase domain (Tran et al., J Biol Chem, 2005, 280, 16244; Wellbrock, C., Nature Reviews Molecular Cell Biology, 2004, 5, 875).

The tissues where the three subclasses of Raf protein are expressed are different. C-Raf is expressed in substantially all tissues, A-Raf is mainly expressed in urogenital (kidney, uterine, and prostate) tissues, and B-Raf is mainly expressed in nervous, spleen, and hematopoietic tissues (Jaiswal, R. K. et al., J. Biol. Chem., 1966, 271, 23626). The overexpression of C-Raf is observed at about 50% in kidney cancer (renal cell carcinoma) and at about 100% in liver cancer (HCC), without expression of oncogenic mutant species.

Vascular endothelial growth factor receptors (VEGFR) are receptor tyrosine kinases (RTK), and are important modulators of angiogenesis. VEGFR is involved in angiogenesis, lymphangiogenesis, and homeostasis, and also has an important influence on neurons. VEGF is mainly produced in vascular endothelial cells, hematoblasts, and stromal cells by hypoxia and the stimulation of cell growth factors such as TGF, interleukin, and PDGF. VEGF binds to VEGF receptors (VEGFR)-1, (VEGFR)-2, and (VEGFR)-3, and each VEGF isoform binds to specific receptors to induce the formation of homozygotes or heterozygotes of the receptors, and then activates each signal transduction pathway. The signal specificity of VEGFR is controlled more minutely by coreceptors such as neurophilin, heparan sulfate, integrin, cadherin, etc.

The biological function of VEGF is mediated through type III RTK, VEGFR-1 (Flt-1), VEGFR-2 (KDR/Flk-1), and VEGFR-3 (Flt-4). EGFR is closely related to Fms, Kit, and PDGFR, and each VEGF binds to specific receptors, wherein VEGF-A binds to VEGFR-1, VEGFR-2 and receptor heteromers, while VEGF-C binds to VEGF-2 and VEGFR-3. Further, PlGF and VEGF-B exclusively interact with VEGFR-1, and VEGF-E interacts only with VEGFR-2. VEGF-F variants interact with VEGFR-1 or VEGFR-2. VEGF-A, VEGF-B, and PlGF are preferentially required for angiogenesis, while VEGF-C and VEGF-D are essential for lymphangiogenesis. New blood vessels feed nutrients and oxygen to tumors and provides a passage of cancer metastasis, and thus are essential for proliferation and metastasis. Angiogenesis normally maintains a balance in the body by the mutual regulation of angiogenic stimulators and angiogenic suppressors, but if such a balance is broken as in cancer cells, the receptor VEGFR is activated by vascular endothelial growth factor (VEGF) that has the greatest influence on vascular endothelial cells.

Among various action mechanisms, inhibitors suppressing VEGF receptor tyrosine kinase using low molecular synthetic material are being variously studied and developed, and most of them have a possibility of being commonly used for solid tumors and suppress angiogenesis activated only in cancer cells, and thus have advantages in that medicinal effects can be expected with relatively few side effects.

DETAILED DESCRIPTION OF THE INVENTION

Technical Problem

It is an object of the present invention to provide novel thienodiazepine derivatives, and pharmaceutically acceptable salts thereof, that exhibit selective inhibition activities against protein kinases.

It is another object of the present invention to provide a pharmaceutical composition for prevention or treatment of abnormal cell growth diseases, containing the thienodiazepine derivatives or pharmaceutically acceptable salts thereof as an active ingredient.

Technical Solution

According to one aspect of the present invention, a thienodiazepine derivative represented by the following Chemical Formula 1 or a pharmaceutically acceptable salt thereof is provided.

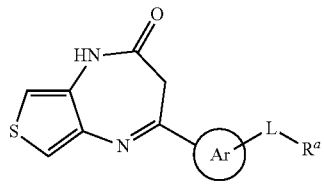

[Chemical Formula 1]

In Chemical Formula 1,
Ar is substituted or unsubstituted C6-20 arylene or substituted or unsubstituted C5-20 heteroarylene;
L is —NR$^1$—C(=O)—, —C(=O)—NR$^1$—, —C(=O)—NR$^1$—C(=O)—, —NR$^1$—C(=O)—NR$^2$—, or —NR$^1$—C(=O)—NR$^2$—C(=O)—;
R$^1$ and R$^2$ are each independently hydrogen, a C1-5 alkyl, a C2-6 unsaturated alkyl, or a C1-5 alkylamine; and
R$^a$ is a C6-20 aryl, a C7-20 alkylaryl, a C7-20 arylalkyl, a C5-20 heteroaryl, a C3-20 cycloalkyl, or a C3-20 heterocycloalkyl, and at least one hydrogen included in R$^a$ is unsubstituted or substituted with a halogen, a halogenated alkyl, a hydroxy group, a carbonyl group, a cyano group, an alkoxy group, a C3-20 heterocycloalkyl group, or a C6-20 aryl group.

According to another aspect of the present invention, a pharmaceutical composition for prevention or treatment of abnormal cell growth diseases, including the above-described thienodiazepine derivative or a pharmaceutically acceptable salt thereof as an active ingredient, is provided.

Hereinafter, thienodiazepine derivatives or pharmaceutically acceptable salts thereof, and a pharmaceutical composition including the same as an active ingredient according to the embodiments of the present invention, will be explained in detail.

Prior to this, technical terms in the present specification are only for mentioning specific embodiments, and they are not intended to restrict the present invention unless explicitly stated.

Further, singular expressions used herein may include plural expressions unless they are differently expressed contextually.

In addition, the meaning of the term "comprise" used in the specification embodies specific characteristics, areas, essences, steps, actions, elements, and/or components, and does not exclude existence or addition of other specific characteristics, areas, essences, steps, actions, elements, components, and/or groups.

I. Thienodiazepine Derivatives or Pharmaceutically Acceptable Salts Thereof

According to one aspect of the present invention, a thienodiazepine derivative represented by the following Chemical Formula 1 or a pharmaceutically acceptable salt thereof is provided.

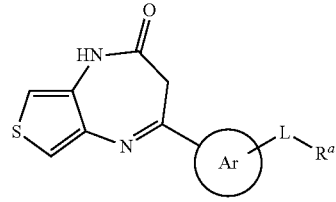

[Chemical Formula 1]

In Chemical Formula 1,
Ar is a substituted or unsubstituted C6-20 arylene or a substituted or unsubstituted C5-20 heteroarylene;
L is —NR$^1$—C(=O)—, —C(=O)—NR$^1$—, —C(=O)—NR$^1$—C(=O)—, —NR$^1$—C(=O)—NR$^2$—, or —NR$^1$—C(=O)—NR$^2$—C(=O)—;
R$^1$ and R$^2$ are each independently hydrogen, a C1-5 alkyl, a C2-6 unsaturated alkyl, or a C1-5 alkylamine; and
R$^a$ is a C6-20 aryl, a C7-20 alkylaryl, a C7-20 arylalkyl, a C5-20 heteroaryl, a C3-20 cycloalkyl, or a C3-20 heterocycloalkyl, and at least one hydrogen included in R$^a$ is unsubstituted or substituted with a halogen, a halogenated alkyl, a hydroxy group, a carbonyl group, a cyano group, an alkoxy group, a C3-20 heterocycloalkyl group, or a C6-20 aryl group.

According to studies of the present inventors, it was confirmed that thienodiazepine derivatives with the structure represented by Chemical Formula 1 exhibit selective inhibition activities against various protein kinases such as c-Kit, FLT3, FMS, LYN, RAF1, VEGFR3, PDGFRa, PDGFRb, RET, etc. It was also confirmed that such thienodiazepine derivatives or pharmaceutically acceptable salts thereof can be used for prevention or treatment of abnormal cell growth diseases.

Those known as protein kinase inhibitors may be classified into type I and type II according to the conformational state of a kinase to which the inhibitor is bound. The type I inhibitors form a hydrogen bond in a hinge region, and thus bind to an ATP-binding site. Meanwhile, although the type II inhibitor binds to an ATP-binding site, it occupies a unique secondary hydrophobic pocket in the non-active region of a kinase. In this respect, approaches to type II inhibitors may have more potential for selective protein kinase inhibitors.

The thienodiazepine derivative represented by Chemical Formula 1 of the present invention has a highly flexible molecular structure due to a linker group (L) positioned between the thienodiazepine moiety and the $R^a$ group of the tail moiety. Thus, since the tail moiety of the thienodiazepine derivative can approach the secondary hydrophobic pocket more easily, it can act as an effective type II inhibitor.

Particularly, the thienodiazepine derivative represented by Chemical Formula 1 has the above-explained structural characteristics, and thus can act as selective inhibitors against kinases such as c-Kit, FLT3, FMS, LYN, RAF1, VEGFR3, PDGFRa, PDGFRb, RET, etc.

Meanwhile, in Chemical Formula 1, Ar is a substituted or unsubstituted C6-20 arylene or a substituted or unsubstituted C5-20 heteroarylene.

Specifically, in the Ar, the acrylene may be a divalent form of an aromatic group such as benzene, biphenylene, triphenylene, naphthalene, anthracene, binaphthylene, phenanthrene, pyrene, dihydropyrene, chrysene, perylene, tetracene, pentacene, benzopyrene, fluorene, indene, indenofluorene, spirobifluorene, etc.

In addition, in the Ar, the heteroarylene may be a divalent form of a heteroaromatic group such as a 5-membered ring (for example, pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, and 1,3,4-thiadiazole); a 6-membered ring (for example, pyridine, pyridazine, pyrimidine, pyrazine, 1,3,5-triazine, 1,2,4-triazine, 1,2,3-triazine, 1,2,4,5-tetrazine, 1,2,3,4-tetrazine, and 1,2,3,5-tetrazine); or a fused group (for example, carbazole, indole, isoindole, indolizine, indazole, benzimidazole, benzotriazole, purine, naphthimidazole, phenanthrimidazole, pyridimidazole, pyrazineimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3-b]thiophene, thieno[3,2-b]thiophene, dithienothiophene, dithienopyridine, isobenzothiophene, dibenzothiophene, benzothiadiazothiophene, etc).

Preferably, the Ar may be 1,4-phenylene, 1,3-phenylene, 1,5-naphthalene, or 2,6-naphthalene.

Further, in Chemical Formula 1, L is a divalent linking group, and is preferably —NR$^1$—C(=O)—, —C(=O)—NR$^1$—, —C(=O)—NR$^1$—C(=O)—, —NR$^1$—C(=O)—NR$^2$—, or —NR$^1$—C(=O)—NR$^2$—C(=O)—. Herein, the R$^1$ and R$^2$ may each independently be hydrogen, a C1-5 alkyl, a C2-6 unsaturated alkyl, or a C1-5 alkylamine.

In Chemical Formula 1, R$^a$ is the end of the —Ar-L-R$^a$ group, and is preferably a C6-20 aryl, a C7-20 alkylaryl, a C7-20 arylalkyl, a C5-20 heteroaryl, a C3-20 cycloalkyl, or a C3-20 hetercycloalkyl. Herein, at least one hydrogen included in R$^a$ may be unsubstituted or substituted with halogen, halogenated alkyl, a hydroxy group, a carbonyl group, a cyano group, an alkoxy group, a C3-20 heterocycloalkyl group, or a C6-20 aryl group.

According to one embodiment of the present invention, the R$^a$ may be 3-chloro-4-(trifluoromethyl)phenyl, 4-chloro-4-(trifluoromethyl)phenyl, 3-(trifluoromethyl)phenyl, 3-(4-methyl-1H-imidazole-1-yl)-5-(trifluoromethyl)phenyl, 3-(morpholin-4-yl)-5-(trifluoromethyl)phenyl, 4-(morpholin-4-yl)-3-(trifluoromethyl)phenyl, 3-(morpholin-4-yl)-4-(trifluoromethyl)phenyl, 3-(morpholin-3-yl)-5-(trifluoromethyl)phenyl, biphenyl-4-yl, biphenyl-2-yl, 1-phenyl-5-(trifluoromethyl)-pyrazole-4-yl, 1-acetylpiperidin-4-yl, bis(4-chlorophenyl)methyl, 2-chloro-5-(4-chlorobenzyl)phenyl, pyridinyl, pyrazinyl, 6-fluorophenyl-methyl, 3-(4-methylpiperazine-1-yl)-5-(trifluoromethyl)phenyl), 3-(4-hydroxylpiperazine-1-yl)-5-(trifluoromethyl)phenyl, 4-(4-ethylpiperazine-1-yl)-3-(trifluoromethyl)phenyl, 4-((4-ethylpiperazine-1-yl)methyl)-3-(trifluoromethyl)phenyl, 4-(1-methylpiperazine-4-yloxy)-3-(trifluoromethyl)phenyl, chlorophenyl, 1H-indol-3-yl-methyl, 2-[(2-cyanophenyl)sulfanyl]phenyl, quinolinyl, biphenyl-4-yl-methyl, 2,4-dimethylphenyl, 6-hydroxy-2,5,7,8-tetramethyl-3,4-dihydro-2H-chromen-2-yl, 2,3-dichlorophenyl, 4-[(4-ethylpiperazine-1-yl)methyl]-3-(trifluoromethyl)phenyl, fluorophenyl, 1H-benzotriazol-5-yl, 5-(4-methoxyphenyl)furan-2-yl, dihydro-1H-indol-2-yl, 3,4-di-methoxyphenyl)methyl, naphthyl, benzothienyl, pyranyl, isoxazolyl, pyrazolyl, pyridazinyl, thiazolyl, thienyl, pyrimidinyl, imidazolyl, pyrolyl, dihydropyrolyl, oxazolyl, triazolyl, thidiazolyl, benzimidazolyl, quinolyl, tetrahydroquinolyl, benzothiazolyl, benzothiazophenyl, benzodioxolyl, indolyl, or dihydrobenzofuranyl.

The terms used in the definition of Chemical Formula 1 are as follows.

An aryl means a monovalent monocyclic, bicyclic, or tricyclic aromatic hydrocarbon moiety having C6-20, preferably C6-15 ring carbons, and it includes a compound in which two or more aromatic hydrocarbons are linked.

An alkylaryl means the above-defined aryl group of which one or more hydrogen atoms are substituted with an alkyl group.

An arylalkyl means an alkyl group of which one or more hydrogen atoms are substituted with an aryl group.

A cycloalkyl means a saturated or unsaturated non-aromatic monovalent monocyclic, bicyclic, or tricyclic hydrocarbon moiety having 3 to 20, preferably 3 to 12, ring carbons.

A heterocycloalkyl means the above-defined cycloalkyl group of which carbon atom is substituted with one or more heteroatoms.

A heteroaryl means the above-defined aryl group of which a carbon atom is substituted with one or more heteroatoms.

An alkoxy means a group in which 1-10, preferably 1-6, linear or branched saturated monovalent hydrocarbons are bonded with oxygen through a single bond.

A heteroatom means an atom other than carbon and oxygen.

According to the embodiment of the invention, representative examples of the thienodiazepine derivative represented by Chemical Formula 1 may include the following compounds. However, the scope of the present invention is not limited to the following compounds.

4-chloro-N-(4-(2-oxo-2,3-dihydro-1H-thieno[3,4-b][1,4]diazepine-4-yl)phenyl)-3-(trifluoromethyl)benzamide;

3-(4-methyl-1H-imidazol-1-yl)-N-(4-(2-oxo-2,3-dihydro-1H-thieno[3,4-b][1,4]diazepine-4-yl)phenyl)-5-(trifluoromethyl)benzamide;

3-morpholino-N-(4-(2-oxo-2,3-dihydro-1H-thieno[3,4-b][1,4]diazepine-4-yl)phenyl)-5-(trifluoromethyl)benzamide;

4-morpholino-N-(4-(2-oxo-2,3-dihydro-1H-thieno[3,4-b][1,4]diazepine-4-yl)phenyl)-3-(trifluoromethyl)benzamide N-(4-(2-oxo-2,3-dihydro-1H-thieno[3,4-b][1,4]diazepine-4-yl)phenyl)biphenyl-4-carboxamide;

N-(4-(2-oxo-2,3-dihydro-1H-thieno[3,4-b][1,4]diazepine-4-yl)phenyl)biphenyl-2-carboxamide;
N-(4-(2-oxo-2,3-dihydro-1H-thieno[3,4-b][1,4]diazepine-4-yl)phenyl)-1-phenyl-5-(trifluoromethyl)-1H-pyrazole-4-carboxamide;
1-acetyl-N-(4-(2-oxo-2,3-dihydro-1H-thieno[3,4-b][1,4]diazepin-4-yl)phenyl)piperidine-4-carboxamide;
2,2-bis(4-chlorophenyl)-N-(4-(2-oxo-2,3-dihydro-1H-thieno[3,4-b][1,4]diazepine-4-yl)phenyl)acetamide;
N-(4-(2-oxo-2,3-dihydro-1H-thieno[3,4-b][1,4]diazepine-4-yl)phenyl)isonicotinamide;
N-(4-(2-oxo-2,3-dihydro-1H-thieno[3,4-b][1,4]diazepine-4-yl)phenyl)pyrazine-2-carboxamide;
3-(4-methylpiperazine-1-yl)-N-(4-(2-oxo-2,3-dihydro-1H-thieno[3,4-b][1,4]diazepine-4-yl)phenyl)-5-(trifluoromethyl)benzamide;
4-chloro-N-(4-(2-oxo-2,3-dihydro-1H-thieno[3,4-b][1,4]diazepin-4-yl)phenyl)benzamide;
2-(1H-indol-3-yl)-N-(4-(2-oxo-2,3-dihydro-1H-thieno[3,4-b][1,4]diazepine-4-yl)phenyl)acetamide;
2-(2-cyanophenylthio)-N-(4-(2-oxo-2,3-dihydro-1H-thieno[3,4-b][1,4]diazepine-4-yl)phenyl)benzamide;
2-(biphenyl-4-yl)-N-(4-(2-oxo-2,3-dihydro-1H-thieno[3,4-b][1,4]diazepine-4-yl)phenyl)acetamide;
3,5-dimethyl-N-(4-(2-oxo-2,3-dihydro-1H-thieno[3,4-b][1,4] diazepine-4-yl)phenyl)benzamide;
4-chloro-N-(3-(2-oxo-2,3-dihydro-1H-thieno[3,4-b][1,4]diazepine-4-yl)phenyl)-3-(trifluoromethyl)benzamide;
3-(4-methyl-1H-imidazol-1-yl)-N-(3-(2-oxo-2,3-dihydro-1H-thieno[3,4-b][1,4]diazepine-4-yl)phenyl)-5-(trifluoromethyl)benzamide;
3-morpholino-N-(3-(2-oxo-2,3-dihydro-1H-thieno[3,4-b][1,4]diazepine-4-yl)phenyl)-5-(trifluoromethyl)benzamide;
4-morpholino-N-(3-(2-oxo-2,3-dihydro-1H-thieno[3,4-b][1,4]diazepine-4-yl)phenyl)-3-(trifluoromethyl)benzamide;
N-(3-(2-oxo-2,3-dihydro-1H-thieno[3,4-b][1,4]diazepine-4-yl)phenyl)biphenyl-4-carboxamide;
N-(3-(2-oxo-2,3-dihydro-1H-thieno[3,4-b][1,4]diazepine-4-yl)phenyl)biphenyl-2-carboxamide;
N-(3-(2-oxo-2,3-dihydro-1H-thieno[3,4-b][1,4]diazepine-4-yl)phenyl)-1-phenyl-5-(trifluoromethyl)-1H-pyrazole-4-carboxamide;
1-acetyl-N-(3-(2-oxo-2,3-dihydro-1H-thieno[3,4-b][1,4]diazepin-4-yl)phenyl)piperidine-4-carboxamide;
2,2-bis(4-chlorophenyl)-N-(3-(2-oxo-2,3-dihydro-1H-thieno[3,4-b][1,4]diazepine-4-yl)phenyl)acetamide;
N-(3-(2-oxo-2,3-dihydro-1H-thieno[3,4-b][1,4]diazepine-4-yl)phenyl)isonicotinamide;
N-(3-(2-oxo-2,3-dihydro-1H-thieno[3,4-b][1,4]diazepine-4-yl)phenyl)pyrazine-2-carboxamide;
3-(4-methylpiperazine-1-yl)-N-(3-(2-oxo-2,3-dihydro-1H-thieno[3,4-b][1,4]diazepine-4-yl)phenyl)-5-(trifluoromethyl)benzamide;
4-chloro-N-(3-(2-oxo-2,3-dihydro-1H-thieno[3,4-b][1,4]diazepine-4-yl)phenyl)benzamide;
2-(1H-indol-3-yl)-N-(3-(2-oxo-2,3-dihydro-1H-thieno[3,4-b][1,4]diazepine-4-yl)phenyl)acetamide;
2-(2-cyanophenylthio)-N-(3-(2-oxo-2,3-dihydro-1H-thieno[3,4-b][1,4]diazepine-4-yl)phenyl)benzamide;
2-(biphenyl-4-yl)-N-(3-(2-oxo-2,3-dihydro-1H-thieno[3,4-b][1,4]diazepine-4-yl)phenyl)acetamide;
3,5-dimethyl-N-(3-(2-oxo-2,3-dihydro-1H-thieno[3,4-b][1,4]diazepine-4-yl)phenyl)benzamide;
2-(2-fluorophenyl)-N-(3-(2-oxo-2,3-dihydro-1H-thieno[3,4-b][1,4]diazepine-4-yl)phenyl)acetamide;
N-(3-(2-oxo-2,3-dihydro-1H-thieno[3,4-b][1,4]diazepine-4-yl)phenyl)quinoline-2-carboxamide;
N-(3-(2-oxo-2,3-dihydro-1H-thieno[3,4-b][1,4]diazepin-4-yl)phenyl)quinoline-3-carboxamide;
(R)-6-hydroxy-2,5,7,8-tetramethyl-N-(3-(2-oxo-2,3-dihydro-1H-thieno[3,4-b][1,4]diazepine-4-yl)phenyl)chroman-2-carboxamide;
1-(4-chloro-3-(trifluoromethyl)phenyl)-3-(4-(2-oxo-2,3-dihydro-1H-thieno[3,4-b][1,4]diazepine-4-yl)phenyl)urea;
1-(4-chlorophenyl)-3-(4-(2-oxo-2,3-dihydro-1H-thieno[3,4-b][1,4]diazepine-4-yl)phenyl)urea;
1-(3-chlorophenyl)-3-(4-(2-oxo-2,3-dihydro-1H-thieno[3,4-b][1,4]diazepine-4-yl)phenyl)urea;
1-(3,4-dichlorophenyl)-3-(4-(2-oxo-2,3-dihydro-1H-thieno[3,4-b][1,4]diazepine-4-yl)phenyl)urea;
1-(4-((4-ethylpiperazine-1-yl)methyl)-3-(trifluoromethyl)phenyl)-3-(4-(2-oxo-2,3-dihydro-1H-thieno[3,4-b][1,4]diazepine-4-yl)phenyl)urea;
1-(3,5-dichlorophenyl)-3-(4-(2-oxo-2,3-dihydro-1H-thieno[3,4-b][1,4]diazepine-4-yl)phenyl)urea;
1-(2-fluorophenyl)-3-(4-(2-oxo-2,3-dihydro-1H-thieno[3,4-b][1,4]diazepine-4-yl)phenyl)urea;
1-(4-chloro-3-(trifluoromethyl)phenyl)-3-(3-(2-oxo-2,3-dihydro-1H-thieno[3,4-b][1,4]diazepine-4-yl)phenyl)urea;
1-(4-chlorophenyl)-3-(3-(2-oxo-2,3-dihydro-1H-thieno[3,4-b][1,4]diazepine-4-yl)phenyl)urea;
1-(3-chlorophenyl)-3-(3-(2-oxo-2,3-dihydro-1H-thieno[3,4-b][1,4]diazepine-4-yl)phenyl)urea;
1-(4-((4-ethylpiperazine-1-yl)methyl)-3-(trifluoromethyl)phenyl)-3-(3-(2-oxo-2,3-dihydro-1H-thieno[3,4-b][1,4]diazepine-4-yl)phenyl)urea;
1-(3,4-dichlorophenyl)-3-(3-(2-oxo-2,3-dihydro-1H-thieno[3,4-b][1,4]diazepine-4-yl)phenyl)urea;
1-(3,5-dichlorophenyl)-3-(3-(2-oxo-2,3-dihydro-1H-thieno[3,4-b][1,4]diazepine-4-yl)phenyl)urea; and
1-(2-fluorophenyl)-3-(3-(2-oxo-2,3-dihydro-1H-thieno[3,4-b][1,4]diazepine-4-yl)phenyl)urea.

Further, the compound represented by Chemical Formula 1 may form a pharmaceutically acceptable salt thereof. Suitable pharmaceutically acceptable salts are those commonly used in the technical field to which the present invention pertains, such as acid addition salts, and are not specifically limited. Preferable acid addition salts may include, for example, inorganic acids such as hydrochloric acid, sulfuric acid, nitric acid, phosphoric acid, perchloric acid, or bromic acid; and organic acids such as acetic acid, methane sulfonic acid, ethane sulfonic acid, p-toluene sulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, or glutamic acid. Organic bases that can be used for the preparation of an organic base addition salt may include tris(hydroxymethyl)methylamine, dicyclohexylamine, etc. Amino acids that can be used for the preparation of an amino acid addition base may include natural amino acids such as alanine, glycine, etc.

The compound represented by Chemical Formula 1 may be provided in the form of a hydrate or a solvate as well as the above-explained pharmaceutically acceptable salt.

The pharmaceutically acceptable salt may be obtained by dissolving the compound represented by Chemical Formula 1 in a solvent miscible with water, such as methanol, ethanol, acetone, and 1,4-dioxane, and adding a free acid or a free base, and then crystallizing it. As non-limiting examples, a specific method of preparing hydrochloric acid addition salt is as shown in Example 26 (synthesis of 2,2-bis(4-chlorophenyl)-N-(3-(2-oxo-2,3-dihydro-1H-thieno[3,4-b][1,4]diazepine-4-yl)phenyl)acetamide described below.

II. Method for Preparing a Thienodiazepine Derivative

According to another aspect of the present invention, a method for preparing a thienodiazepine derivative represented by Chemical Formula 1 is provided.

Specifically, the thienodiazepine derivative represented by Chemical Formula 1 may be prepared according to Schemes 1 to 3 shown in FIG. 1.

First, in Scheme 1 of FIG. 1, a step of obtaining a compound 3a or 3b from a compound 1a or 1b through an intermediate compound 2a or 2b, or a step of obtaining a compound 3a or 3b through the esterification of the compound 2a or 2b, is conducted.

Separately, in Scheme 2 of FIG. 1, a step of obtaining a compound 5 (thiophene-3,4-diamine) by the reduction of a compound 4 (2,5-dibromo-3,4-dinitrothiophene) using Sn in an acid solution, is conducted.

Further, in Scheme 3 of FIG. 1, steps of obtaining a compound 6a or 6b by the condensation of the compound 5 and the compound 3a or 3b, obtaining a compound 7a or 7b by the reduction of the compound 6a or 6b, and obtaining a compound 7a or 8b by the coupling of the compound 7a or 7b with carboxylic acid ($R^x$—$CO_2H$), are conducted. A step of obtaining a compound 9a or 9b by the coupling of the compound 7a or 7b with isocyanate ($R^y$—N=C=O) may also be conducted.

However, the preparation method of the thienodiazepine derivative represented by Chemical Formula 1 is not limited thereto, and it may be conducted by applying and appropriately modifying reactions commonly used in the technical field to which the present invention pertains.

III. Pharmaceutical Composition Including a Thienodiazepine Derivative

Meanwhile, according to yet another aspect of the present invention, a pharmaceutical composition for prevention or treatment of abnormal cell growth diseases, including the above-described thienodiazepine derivative or a pharmaceutically acceptable salt thereof as an active ingredient, is provided.

As explained, the thienodiazepine derivative represented by Chemical Formula 1 has the structural characteristic of a highly flexible molecular structure due to the linker group (L) positioned between the thienodiazepine moiety and the $R^a$ group of the tail moiety. Thus, the tail moiety of the thienodiazepine derivative can approach a secondary hydrophobic pocket more easily. Therefore, the thienodiazepine derivative or a pharmaceutically acceptable salt thereof may exhibit selective inhibition activities against kinases such as c-Kit, FLT3, FMS, LYN, RAF1, VEGFR3, PDGFRa, PDGFRb, RET, etc., and can be used in a pharmaceutical composition for prevention or treatment of abnormal cell growth diseases.

The thienodiazepine derivative represented by Chemical Formula 1 or a pharmaceutically acceptable salt thereof may exhibit selective inhibition activities against various protein kinases inducing abnormal cell growth diseases. For example, the thienodiazepine derivative represented by Chemical Formula 1 or a pharmaceutically acceptable salt thereof may exhibit inhibition activities against c-Kit, FLT3, FMS, LYN, RAF1, VEGFR3, PDGFRa, PDGFRb, RET, etc., which are known to induce stomach cancer, lung cancer, liver cancer, colorectal cancer, small bowel cancer, pancreatic cancer, brain cancer, bone cancer, melanoma, breast cancer, sclerosing adenosis, uterine cancer, uterine cervical cancer, head and neck cancer, esophageal cancer, thyroid cancer, parathyroid cancer, kidney cancer, sarcoma, prostate cancer, urethral cancer, bladder cancer, blood cancer such as leukemia, multiple myeloma, and myelodysplastic syndrome, lymphoma such as Hodgkin's disease and non-Hodgkin's lymphoma, psoriasis, fibroadenoma, etc.

The pharmaceutical composition including the thienodiazepine derivative or a pharmaceutically acceptable salt thereof according to the present invention as an active ingredient may be formulated in a form for oral or parenteral administration according to standard pharmaceutical practice. These dosage forms may contain additives such as pharmaceutically acceptable carriers, adjuvants, diluents, etc., in addition to the active ingredient. When formulated, additives or excipients such as commonly used fillers, bulking agents, binders, wetting agents, disintegrating agents, surfactants, etc. may be used.

A solid formulation for oral administration includes a tablet, a pill, a powder, granules, a capsule, troches, etc., and such a solid formulation may be prepared by mixing the compound of Chemical Formula 1 according to the present invention, or a pharmaceutically acceptable salt, a hydrate, or a solvate thereof, with at least one excipient, for example, starch, calcium carbonate, sucrose, lactose, gelatin, etc.

A liquid formulation for oral administration includes a suspension, a liquid for internal use, an emulsion or syrup, etc., and it may include various excipients, for example, a wetting agent, a sweetener, a flavoring agent, a preservative, etc., in addition to commonly used diluents such as water and liquid paraffin.

A formulation for parenteral administration includes a sterilized aqueous solution, a non-aqueous solution, a suspended solution, an emulsion, a lyophilized preparation, a suppository, etc. As the non-aqueous solution and the suspended solution, propylene glycol, polyethylene glycol, a vegetable oil such as olive oil, an injectable ester such as ethyl oleate, etc. may be used.

The preferable amount of administration of the thienodiazepine represented by Chemical Formula 1 or a pharmaceutically acceptable salt thereof may vary according to the conditions and body weight of a patient, the severity of disease, the form of drug, and the route and period of administration, but it may be appropriately selected by a method commonly used in the technical field to which the present invention pertains. The pharmaceutical composition according to the present invention may be administered to mammals including rats, mice, domestic animals, and human beings by various routes. All usual administration routes may be expected, and for example, it may be administered orally, rectally, intravenously, intramuscularly, subcutaneously, intrauterinally, or intracerebroventricularly.

The thienodiazepine represented by Chemical Formula 1 or a pharmaceutically acceptable salt thereof may have activities in and of itself, or after being absorbed into a body, and pharmacological effects may be exhibited by special body's environment or metabolites, etc., and may exhibit pharmacological effects as an agonist.

Advantageous Effects

The thienodiazepine derivatives or pharmaceutically acceptable salts thereof according to the present invention exhibit selective inhibition activities against various protein kinases, thus inhibiting proliferation of abnormal cells, and particularly, exhibit high inhibition rates against c-Kit, FLT3, FMS, LYN, RAF1, VEGFR3, PDGFRa, PDGFRb, RET, etc., and thus can be used as a pharmaceutical composition for prevention or treatment of abnormal cell growth diseases.

BRIEF DESCRIPTION OF THE DRAWING

FIG. 1 shows schemes for the synthesis of the thienodiazepine derivative according to one embodiment of the present invention.

DETAILED DESCRIPTION OF THE EMBODIMENTS

Hereinafter, the actions and effects of the invention will be explained through specific examples. However, these examples are presented only as the illustrations of the invention, and the scope of the invention is not limited thereby.

EXAMPLE 1

Synthesis of 4-chloro-N-(4-(2-oxo-2,3-dihydro-1H-thieno[3,4-b][1,4]diazepine-4-yl)phenyl)-3-(trifluoromethyl)benzamide (Step 1) Synthesis of 2,2-dimethyl-5-(4-nitrobenzoyl)-1,3-dioxane-4,6-dione

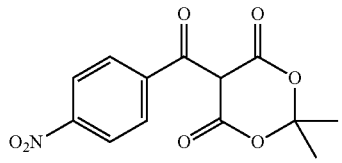 [SMILES: CC1(C)OC(=O)C(C(=O)c2ccc([N+](=O)[O-])cc2)C(=O)O1]

Meldrum's acid (3 g, 20.8 mmol) and N,N-dimethyl amino pyridine (4.8 g, 26 mmol) were dissolved in methylene chloride, nitrobenzoyl chloride (5 g, 42 mmol) was then slowly dripped thereto, and the solution was stirred for 4 hours. After the completion of the reaction was confirmed, it was extracted three times with methylene chloride and washed with water, and then dried with anhydrous magnesium sulfate and filtered. The filtrate was distilled under reduced pressure, and the concentrated residue was purified and separated through column chromatography (silica gel, methylene chloride: MeOH=10:1) to obtain a target compound B (2,2-dimethyl-5-(4-nitrobenzoyl)-1,3-dioxane-4,6-dione, 2.3 g, 40%).

(Step 2) Synthesis of ethyl 3-(4-nitrophenyl)-3-oxopropanoate

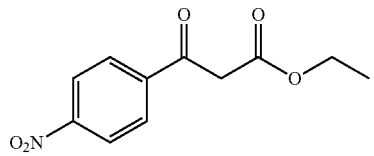 [SMILES: CCOC(=O)CC(=O)c1ccc([N+](=O)[O-])cc1]

The compound B (2.3 g, 7.8 mmol) was dissolved in EtOH and then stirred under reflux at 100° C. for 10 hours. After the completion of the reaction was confirmed, the solvent was removed under reduced pressure, the filtrate was distilled under reduced pressure, and the concentrated residue was purified and separated through column chromatography (silica gel, methylene chloride) to obtain a target compound C (ethyl 3-(4-nitrophenyl)-3-oxopropanoate, 1.7 g, 83%).

$^1$H NMR (400 MHz, CDCl$_3$) δ 8.27 (2 H, d, J=9.2), 7.93 (2 H, d, J=9.2), 5.76 (1 H, s), 4.30 (2 H, q, J=7.2), 1.35 (3 H, t, J=7.2)

(Step 3) Synthesis of thiophene-3,4-diamine

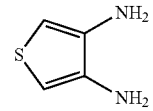

2,5-dibromo-3,4-dinitrothiophene 4a (1.8 g, 5.4 mmol) was dissolved in HCl (23 ml), and then tin metal (4.5 g, 37.8 mmol) was slowly added thereto. After the completion of the reaction was confirmed, the solution was filtered to obtain a white precipitate, and then pH was adjusted to about 7~8 while slowly introducing an aqueous solution of KOH, thus obtaining a target compound D (thiophene-3,4-diamine, 172.8 mg, 29%).

$^1$H NMR (400 MHz, DMSO-d$_6$) δ 8.29 (d, J=1.6 Hz, 1 H), 8.06 (d, J=8.8 Hz, 1 H), 7.67 (dd, J=1.6, 8.8 Hz, 1 H), 4.47 (q, J=7.2 Hz, 2 H), 1.41 (t, J=7.2 Hz, 3 H).

(Step 4) Synthesis of 4-(4-nitrophenyl)-1H-thieno[3,4-b][1,4]diazepine-2(3H)-one

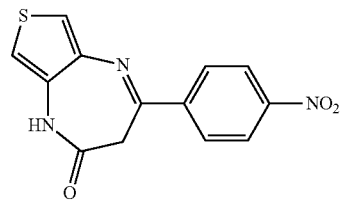 [SMILES: O=C1CC(c2ccc([N+](=O)[O-])cc2)=Nc2cscc2N1]

The compound C (239 mg, 1.0 mmol) and the compound D (172.8 mg, 1.5 mmol) obtained in the above processes were dissolved in xylene, reacted in a 500 W microwave for 10 minutes, and the reaction mixture was extracted with methylene chloride three times and washed with water and then dried with anhydrous magnesium sulfate and filtered. The filtrate was distilled under reduced pressure, and the concentrated residue was purified and separated through column chromatography (silica gel, ethyl acetate:hexane=1:1) to obtain a target compound E (4-(4-nitrophenyl)-1H-thieno[3,4-b][1,4]diazepine-2(3H)-one, 244 mg, 56%).

$^1$H NMR (400 MHz, DMSO-d$_6$) δ 8.94 (1 H, t, J=1.6 Hz), 8.37-8.32 (2 H, m), 8.23 (1 H, s), 7.66 (1 H, t, J=8.0 Hz), 7.45 (1 H, d, J=3.6 Hz), 6.91 (1 H, d, J=3.6 Hz), 3.73 (2 H, s)

$^1$H NMR (400 MHz, DMSO-d$_6$) δ 10.59 (1 H, s), 8.36 (2 H, d, J=8.8 Hz), 8.24 (2 H, d, J=8.8 Hz), 7.65 (1 H, d, J=3.6 Hz), 7.06 (1 H, d, J=3.6 Hz), 3.67 (2 H, s)

(Step 5) Synthesis of 4-(4-aminophenyl)-1H-thieno
[3,4-b][1,4]diazepine-2(3H)-one

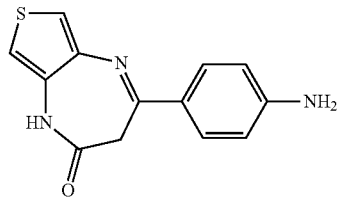 [SMILES: Nc1ccc(C2=Nc3cscc3NC(=O)C2)cc1]

The above-obtained compound E (224 mg, 0.8 mmol) and ammonium chloride (165.8 mg, 3.1 mmol) were dissolved in 4 ml of ammonium chloride:water (3:1), and then Fe (173.1 mg, 3.1 mmol) was added thereto. After the completion of the reaction was confirmed, the solvent was removed under reduced pressure, and the reaction mixture was extracted with methylene chloride three times and washed with water, and then dried with anhydrous magnesium sulfate and filtered. The filtrate was distilled under reduced pressure, and the concentrated residue was purified and separated through column chromatography (silica gel, methylene chloride:MeOH=10:1) to obtain a target compound F (4-(4-aminophenyl)-1H-thieno[3,4-b][1,4]diazepine-2(3H)-one, 178 mg, 87%).

$^1$H NMR (400 MHz, DMSO-$d_6$) δ 10.50 (1 H, s), 7.45 (1 H, d, J=3.6 Hz), 7.26 (1H, t, J=4.0 Hz), 7.14-7.12 (2 H, m), 6.99 (1 H, d, J=3.6 Hz), 5.30 (2 H, s), 3.50 (2 H, s)

$^1$H NMR (400 MHz, DMSO-$d_6$) δ 10.34 (1 H, s), 7.45 (2 H, d, J=8.4 Hz), 7.31 (1 H, d, J=3.6 Hz), 6.95 (1 H, d, J=4.0 Hz), 6.61 (2 H, d, J=8.8 Hz), 5.79 (2 H, s), 3.50 (2 H, s)

(Step 6) Synthesis of 4-chloro-N-(4-(2-oxo-2,3-
dihydro-1H-thieno[3,4-b][1,4]diazepine-4-yl)phe-
nyl)-3-(trifluoromethyl)benzamide

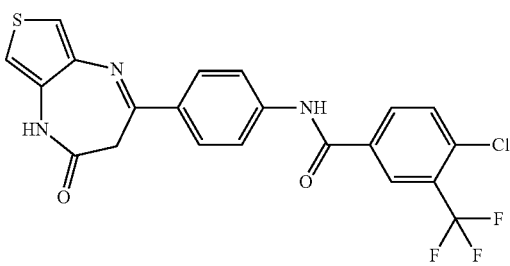 [SMILES: O=C1CC(c2ccc(NC(=O)c3ccc(Cl)c(C(F)(F)F)c3)cc2)=Nc2cscc2N1]

The above-obtained compound F (22 mg), 3-trifluoromethyl-4-chloro benzoic acid (35.2 mg), EDCl (40.6 mg), HOBt (25 mg), and triethylamine (40 μL) were dissolved in a solvent of N,N-dimethylformamide, and then the solution was stirred at 70° C. for 12 hours. After cooling it to room temperature, ethyl acetate was added thereto, followed by washing with an aqueous solution of sodium bicarbonate. The organic layer was dried with sodium sulfite and filtered, and then the solvent was removed under reduced pressure. The residue was recrystallized with ethyl acetate and hexane to obtain a target compound 4-chloro-N-(4-(2-oxo-2,3-dihydro-1H-thieno[3,4-b][1,4]diazepine-4-yl)phenyl)-3-(trifluoromethyl)benzamide (18 mg, 92%).

$^1$H NMR (400 MHz, DMSO-$d_6$) δ 10.79 (1 H, s), 10.52 (1 H, s), 8.42 (1 H, d, J=2.0 Hz), 8.29 (1 H, dd, J=8.2 Hz), 8.07 (2 H, d, J=8.8 Hz), 7.94 (3 H, m), 7.51 (1 H, d, J=3.6 Hz), 7.02 (1 H, d, J=3.6 Hz), 3.61 (2 H, s)
(m/z 464.0431)

Example 2

Synthesis of 3-(4-methyl-1H-imidazol-1-yl)-N-(4-
(2-oxo-2,3-dihydro-1H-thieno[3,4-b][1,4]diazepine-
4-yl)phenyl)-5-(trifluoromethyl)benzamide

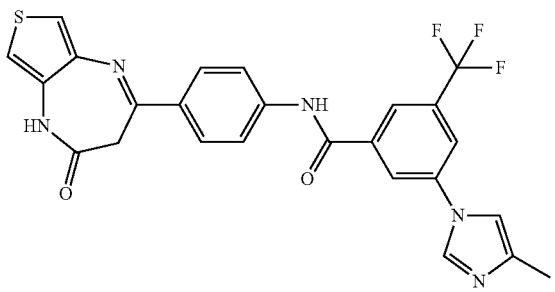 [SMILES: Cc1cn(-c2cc(C(=O)Nc3ccc(C4=Nc5cscc5NC(=O)C4)cc3)cc(C(F)(F)F)c2)cn1]

3-(4-methyl-1H-imidazol-1-yl)-5-(trifluoromethyl)benzoic acid (10 mg, 0.030 mmol), 1-[bis(dimethylamino)methylene]-1H-1,2,3-triazolo[4,5-b]pyridinium 3-oxid hexafluorophosphate (22 mg, 0.058 mmol), and TEA (7.9 mg, 0.078 mmol) were dissolved in DMF (0.2 ml), the solution was stirred at 45° C. for 30 minutes, and then the compound F (10 mg, 0.030 mmol) was added, followed by stirring the solution at 45° C. for 12 hours. After the reaction was completed, ethyl acetate was added, and the reaction mixture was washed with a saturated aqueous NaCl solution. The organic layer was dried with sodium sulfate anhydrous and filtered, and then the solvent was removed under reduced pressure. The residue was crystallized to obtain a target compound 3-(4-methyl-1H-imidazol-1-yl)-N-(4-(2-oxo-2,3-dihydro-1H-thieno[3,4-b][1,4]diazepine-4-yl)phenyl)-5-(trifluoromethyl)benzamide (10.3 mg, 67%).

$^1$H NMR (400 MHz, DMSO-$d_6$) δ 10.77 (1 H, s), 10.53 (1 H, s), 8.49 (1 H, s), 8.43 (1 H, s), 8.27 (1 H, s), 8.19 (1 H, s), 8.09 (2 H, d, J=8.8 Hz), 7.95 (2 H, d, J=8.8 Hz), 7.75 (1 H, s), 7.52 (1 H, d, J=4.0 Hz), 7.02 (1 H, d, J=3.6 Hz), 3.61 (2 H, s), 2.19 (3 H, s)
(Exact mass 509.11, m/z 510.1193)

Example 3

Synthesis of 3-morpholino-N-(4-(2-oxo-2,3-di-
hydro-1H-thieno[3,4-b][1,4]diazepine-4-yl)phenyl)-
5-(trifluoromethyl)benzamide

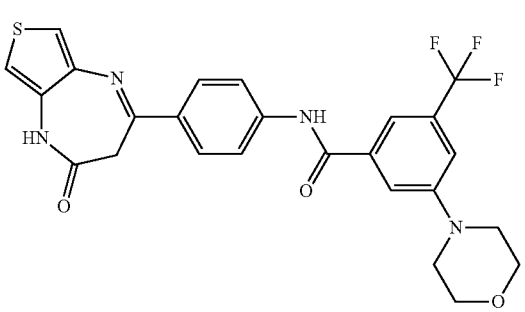 [SMILES: O=C1CC(c2ccc(NC(=O)c3cc(N4CCOCC4)cc(C(F)(F)F)c3)cc2)=Nc2cscc2N1]

3-morpholino-5-(trifluoromethyl)benzoic acid (10.7 mg, 0.038 mmol), 1-[bis(dimethylamino)methylene]-1H-1,2,3-triazolo[4,5-b]pyridinium 3-oxid hexafluorophosphate (22 mg, 0.058 mmol), and TEA (7.9 mg, 0.078 mmol) were dissolved in DMF (0.2 ml), the solution was stirred at 45° C. for 30 minutes, and then the compound F (10 mg, 0.038 mmol) was added thereto, followed by stirring the solution at 45° C. for 12 hours. After the reaction was completed, ethyl acetate was added and the reaction mixture was washed with an aqueous solution of saturated NaCl. The organic layer was dried with sodium sulfate anhydrous and filtered, and then the solvent was removed under reduced pressure. The residue was purified through column chromatography (silica gel, ethyl acetate:Hex=1:1) to obtain a target compound 3-morpholino-N-(4-(2-oxo-2,3-dihydro-1H-thieno[3,4-b][1,4]diazepine-4-yl)phenyl)-5-(trifluoromethyl)benzamide (10 mg, 51%).

$^1$H NMR (400 MHz, DMSO-$d_6$) δ 10.59 (1 H, s), 10.48 (1 H, s), 8.06 (2 H, d, J=8.8 Hz), 7.93 (2 H, d, J=8.8 Hz), 7.74 (1 H, s), 7.68 (1 H, s), 7.50 (1 H, d, J=8.8 Hz), 7.41 (1 H, s), 7.02 (1 H, d, J=8.8 Hz), 3.78 (4 H, t, J=4.8 Hz), 3.61 (2 H, s)

(Exact mass 514.13, m/z 515.1342)

Example 4

Synthesis of 4-morpholino-N-(4-(2-oxo-2,3-dihydro-1H-thieno[3,4-b][1,4]diazepine-4-yl)phenyl)-3-(trifluoromethyl)benzamide

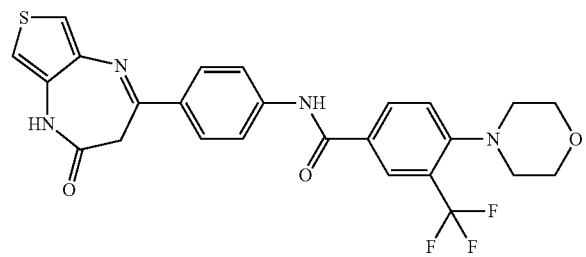 [SMILES: O=C1CC(c2ccc(NC(=O)c3ccc(N4CCOCC4)c(C(F)(F)F)c3)cc2)=Nc2cscc2N1]

4-morpholino-3-(trifluoromethyl)benzoic acid (10.7 mg, 0.038 mmol), 1-[bis(dimethylamino)methylene]-1H-1,2,3-triazolo[4,5-b]pyridinium 3-oxid hexafluorophosphate (22 mg, 0.058 mmol), and TEA (7.9 mg, 0.078 mmol) were dissolved in DMF (0.2 ml), the solution was stirred at 45° C. for 30 minutes, and then the compound F (10 mg, 0.038 mmol) was added, followed by stirring the solution at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 4-morpholino-N-(4-(2-oxo-2,3-dihydro-1H-thieno[3,4-b][1,4]diazepine-4-yl)phenyl)-3-(trifluoromethyl)benzamide (15.1 mg, 77%).

$^1$H NMR (400 MHz, DMSO-$d_6$) δ 10.60 (1 H, s), 10.48 (1 H, s), 8.28-8.26 (2 H, m), 8.05 (2 H, d, J=8.8 Hz), 7.93 (2 H, d, J=8.8 Hz), 7.67 (1 H, d, J=8.0 Hz), 7.50 (1 H, d, J=3.6 Hz), 7.02 (1 H, d, J=3.6 Hz), 3.74 (4 H, t, J=4.4 Hz), 3.60 (2 H, s), 2.98 (4 H, t, J=4.2 Hz)

(Exact mass 514.13, m/z 515.1344)

Example 5

Synthesis of N-(4-(2-oxo-2,3-dihydro-1H-thieno[3,4-b][1,4]diazepine-4-yl)phenyl)biphenyl-4-carboxamide

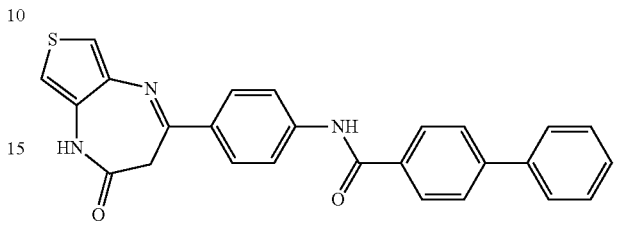

2-(biphenyl-4-yl)acetic acid (9 mg, 0.045 mmol), 1-[bis(dimethylamino)methylene]-1H-1,2,3-triazolo[4,5-b]pyridinium 3-oxid hexafluorophosphate (21.7 mg, 0.057 mmol), and TEA (7.7 mg, 0.076 mmol) were dissolved in DMF (0.2 ml), the solution was stirred at 45° C. for 30 minutes, and then the compound F (10 mg, 0.038 mmol) was added thereto, followed by stirring the solution at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(4-(2-oxo-2,3-dihydro-1H-thieno[3,4-b][1,4]diazepine-4-yl)phenyl)biphenyl-4-carboxamide (9.4 mg, 56%).

$^1$H NMR (400 MHz, DMSO-$d_6$) δ 10.54 (1 H, s), 10.52 (1 H, s), 8.48 (1 H, s), 8.11 (2 H, d, J=8.4 Hz), 8.04 (1 H, d, J=7.2 Hz), 7.86 (2 H, d, J=8.8 Hz), 7.79-7.75 (3 H, m), 7.55-7.52 (4 H, m), 7.43 (1 H, d, J=7.2 Hz), 7.04 (1 H, d, J=4.0 Hz), 3.61 (2 H, s), 3.62 (2 H, s)

(Exact mass 437.12, m/z 438.1254)

Example 6

Synthesis of N-(4-(2-oxo-2,3-dihydro-1H-thieno[3,4-b][1,4]diazepine-4-yl)phenyl)biphenyl-2-carboxamide

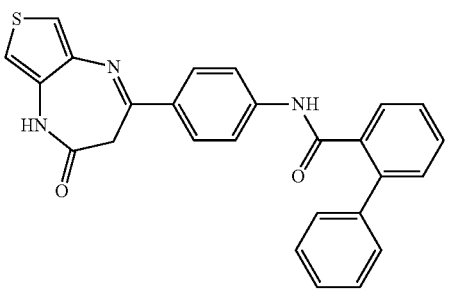 [SMILES: O=C1CC(c2ccc(NC(=O)c3ccccc3-c3ccccc3)cc2)=Nc2cscc2N1]

Biphenyl-2-carboxylic acid (8.3 mg, 0.041 mmol), 1-[bis(dimethylamino)methylene]-1H-1,2,3-triazolo[4,5-b]pyridinium 3-oxid hexafluorophosphate (21.7 mg, 0.057 mmol), and TEA (7.7 mg, 0.076 mmol) were dissolved in DMF (0.2 ml), followed by stirring the solution at 45° C. for 30 minutes, and then the compound F (9.8 mg, 0.038 mmol) was added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(4-(2-oxo-2,3-dihydro-1H-thieno[3,4-b][1,4]diazepine-4-yl)phenyl) biphenyl-2-carboxamide (8 mg, 48%).

$^1$H NMR (400 MHz, DMSO-d$_6$) δ 10.51 (1 H, s), 10.47 (1 H, s), 7.94 (2 H, d, J=8.8 Hz), 7.66 (2 H, d, J=8.8 Hz), 7.62-7.57 (2 H, m), 7.53-7.47 (3 H, m), 7.45-7.43 (2 H, m), 7.37 (2 H, t, J=7.6 Hz), 7.31-7.27 (1 H, m), 7.00 (1 H, d, J=3.6 Hz), 3.56 (2 H, s)

(Exact mass 437.12, m/z 438.1254)

Example 7

Synthesis of N-(4-(2-oxo-2,3-dihydro-1H-thieno[3,4-b][1,4]diazepine-4-yl)phenyl)-1-phenyl-5-(trifluoromethyl)-1H-pyrazole-4-carboxamide

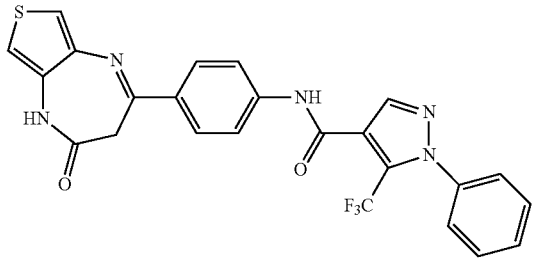 [SMILES: O=C1CC(c2ccc(NC(=O)c3cnn(-c4ccccc4)c3C(F)(F)F)cc2)=Nc2cscc2N1]

1-phenyl-5-(trifluoromethyl)-1H-pyrazole-4-carboxylic acid (10 mg, 0.039 mmol), 1-[bis(dimethylamino)methylene]-1H-1,2,3-triazolo[4,5-b]pyridinium 3-oxid hexafluorophosphate (20 mg, 0.052 mmol), and TEA (7.1 mg, 0.070 mmol) were dissolved in DMF (0.3 ml), the solution was stirred at 45° C. for 30 minutes, the compound F (9.1 mg, 0.035 mmol) was added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(4-(2-oxo-2,3-dihydro-1H-thieno[3,4-b][1,4]diazepine-4-yl)phenyl)-1-phenyl-5-(trifluoromethyl)-1H-pyrazole-4-carboxamide (4.5 mg, 27%).

$^1$H NMR (400 MHz, DMSO-d$_6$) δ 10.78 (1 H, s), 10.47 (1 H, s), 8.36 (1 H, s), 8.05 (2 H, d, J=8.8 Hz), 7.87 (2 H, d, J=8.8 Hz), 7.63-7.61 (3 H, m), 7.56-7.55 (2 H, m), 7.50 (1 H, d, J=4.0 Hz), 7.02 (1 H, d, J=3.6 Hz)

(Exact mass 495.10, m/z 496.1016)

Example 8

Synthesis of 1-acetyl-N-(4-(2-oxo-2,3-dihydro-1H-thieno[3,4-b][1,4]diazepine-4-yl)phenyl)piperidine-4-carboxamide

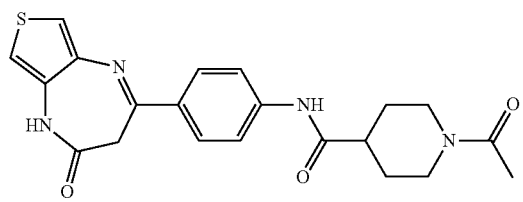 [SMILES: CC(=O)N1CCC(C(=O)Nc2ccc(C3=Nc4cscc4NC(=O)C3)cc2)CC1]

1-acetylpiperidine-4-carboxylic acid (6.9 mg, 0.040 mmol), 1-[bis(dimethylamino)methylene]-1H-1,2,3-triazolo[4,5-b]pyridinium 3-oxid hexafluorophosphate (20.8 mg, 0.056 mmol), and TEA (7.5 mg, 0.070 mmol) were dissolved in DMF (0.3 ml), and the solution was stirred at 45° C. for 30 minutes, and then the compound F (9.4 mg, 0.037 mmol) was added and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 1-acetyl-N-(4-(2-oxo-2,3-dihydro-1H-thieno[3,4-b][1,4]diazepine-4-yl)phenyl)piperidine-4-carboxamide (11 mg, 72%).

$^1$H NMR (400 MHz, DMSO-d$_6$) δ 10.53 (1 H, s), 9.97 (1 H, s), 7.98 (1 H, d, J=8.0 Hz), 7.74 (1 H, d, J=8.0 Hz), 7.47 (1 H, d, J=3.6 Hz), 7.00 (1 H, d, J=3.6 Hz), 4.43-4.39 (1 H, m), 3.89-3.86 (1 H, m), 3.57 (2 H, s), 3.10-3.04 (1 H, m), 2.61-2.59 (2 H, m), 2.01 (3 H, s), 1.85-1.80 (2 H, m), 1.64-1.54 (1 H, m), 1.49-1.39 (1 H, m)

(Exact mass 410.14, m/z 411.1467)

Example 9

Synthesis of 2,2-bis(4-chlorophenyl)-N-(4-(2-oxo-2,3-dihydro-1H-thieno[3,4-b][1,4]diazepine-4-yl)phenyl)acetamide

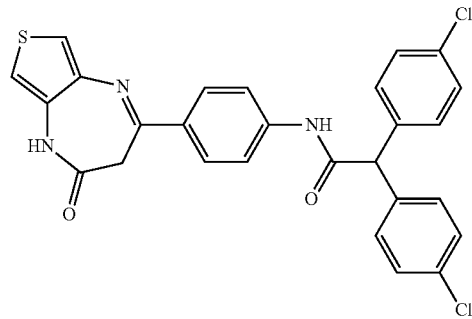 [SMILES: O=C1CC(c2ccc(NC(=O)C(c3ccc(Cl)cc3)c3ccc(Cl)cc3)cc2)=Nc2cscc2N1]

2,2-bis(4-chlorophenyl)acetic acid (10 mg, 0.032 mmol), 1-[bis(dimethylamino)methylene]-1H-1,2,3-triazolo[4,5-b]pyridinium 3-oxid hexafluorophosphate (18.25 mg, 0.048 mmol), and TEA (6.52 mg, 0.064 mmol) were dissolved in DMF (0.2 ml), the solution was stirred at 45° C. for 30 minutes, the compound F (8.3 mg, 0.032 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 2,2-bis(4-chlorophenyl)-N-(4-(2-oxo-2,3-dihydro-1H-thieno[3,4-b][1,4]diazepine-4-yl)phenyl)acetamide (12 mg, 72%).

$^1$H NMR (400 MHz, DMSO-$d_6$) δ 10.71 (1 H, s), 10.45 (1 H, s), 7.99 (2 H, d, J=8.8 Hz), 7.74 (2 H, d, J=8.8 Hz), 7.47 (1 H, d, J=3.6 Hz), 7.42 (4 H, d, J=8.8 Hz), 7.37 (4 H, d, J=8.8 Hz), 7.00 (1 H, d, J=3.6 Hz), 5.23 (1 H, s), 3.56 (2 H, s)

(Exact mass 519.06, m/z 521.0682)

Example 10

Synthesis of N-(4-(2-oxo-2,3-dihydro-1H-thieno[3,4-b][1,4]diazepine-4-yl)phenyl)isonicotinamide

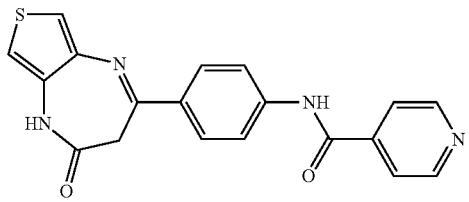 [SMILES: O=C1CC(c2ccc(NC(=O)c3ccncc3)cc2)=Nc2cscc2N1]

The compound F (20 mg, 0.077 mmol), isonicotinoyl chloride (10 mg, 0.077 mmol), and TEA (56 mg, 0.154 mmol) were dissolved in THF (0.64 ml), and then the solution was stirred at 65° C. for 12 hours. After the reaction was completed, ethyl acetate was added, and the reaction mixture was washed with a saturated aqueous NaCl solution. The organic layer was dried with magnesium sulfate anhydrous and filtered, and then the solvent was removed under reduced pressure. The residue was purified through column chromatography (silica gel, ethyl acetate:Hex=1:1) to obtain a target compound N-(4-(2-oxo-2,3-dihydro-1H-thieno[3,4-b][1,4]diazepine-4-yl)phenyl)isonicotinamide (7 mg, 25%).

$^1$H NMR (400 MHz, DMSO-$d_6$) δ 10.76 (s, 1 H), 10.51 (s, 1 H), 8.81 (dd, J=4.6, 1.4 Hz, 2 H), 8.06 (d, J=8.9 Hz, 2 H), 7.94 (d, J=8.9 Hz, 2 H), 7.89 (dd, J=4.5, 1.6 Hz, 2 H), 7.51 (d, J=3.7 Hz, 1 H), 7.02 (d, J=3.7 Hz, 1 H), 3.61 (s, 2 H).

(Exact m/z 362.08, m/z 362.41)

Example 11

Synthesis of N-(4-(2-oxo-2,3-dihydro-1H-thieno[3,4-b][1,4]diazepine-4-yl)phenyl)pyrazine-2-carboxamide

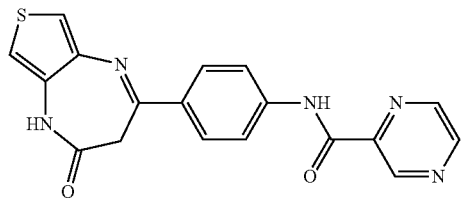 [SMILES: O=C1CC(c2ccc(NC(=O)c3cnccn3)cc2)=Nc2cscc2N1]

Pyrazine-2-carboxylic acid (9.5 mg, 0.077 mmol), 1-[bis(dimethylamino)methylene]-1H-1,2,3-triazolo[4,5-b]pyridinium 3-oxid hexafluorophosphate (43 mg, 0.115 mmol), and TEA (56 mg, 0.154 mmol) were dissolved in DMF (0.64 ml), and the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(4-(2-oxo-2,3-dihydro-1H-thieno[3,4-b][1,4]diazepine-4-yl)phenyl)pyrazine-2-carboxamide (8 mg, 28%).

$^1$H NMR (400 MHz, DMSO-$d_6$) δ 11.00 (1 H, s), 10.50 (1 H, s), 9.33 (1 H, s), 8.96 (1 H, d, J=2.4 Hz), 8.84 (1 H, dd, J=2.5, 1.5 Hz), 8.10-8.03 (4 H, m), 7.51 (1 H, d, J=3.7 Hz), 7.02 (1 H, d, J=3.7 Hz), 3.61 (2 H, s).

(Exact m/z 363.08, m/z 364.08)

Example 12

Synthesis of 3-(4-methylpiperazine-1-yl)-N-(4-(2-oxo-2,3-dihydro-1H-thieno[3,4-b][1,4]diazepine-4-yl)phenyl)-5-(trifluoromethyl)benzamide

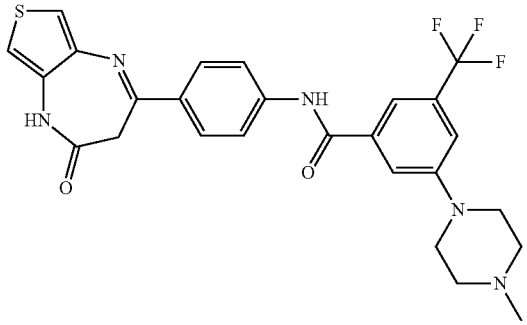 [SMILES: CN1CCN(c2cc(C(=O)Nc3ccc(C4=Nc5cscc5NC(=O)C4)cc3)cc(C(F)(F)F)c2)CC1]

3-(4-methylpiperazine-1-yl)-5-(trifluoromethyl)benzoic acid (54 mg, 0.19 mmol), 1-[bis(dimethylamino)methylene]-1H-1,2,3-triazolo[4,5-b]pyridinium 3-oxid hexafluorophosphate (108 mg, 0.28 mmol), and TEA (3 8 mg, 0.38 mmol) were dissolved in DMF (1.5 ml), the solution was stirred at 45° C. for 30 minutes, the compound F (50 mg, 0.19 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 3-(4-methylpiperazine-1-yl)-N-(4-(2-oxo-2,3-dihydro-1H-thieno[3,4-b][1,4]diazepine-4-yl)phenyl)-5-(trifluoromethyl)benzamide (10 mg, 10%).

$^1$H NMR (400 MHz, DMSO-d$_6$) δ 10.587 (s, 1 H), 10.496 (s, 1 H), 8.03 (d, J=9.2 Hz, 2 H), 7.91 (d, J=9.2 Hz, 2 H), 7.73 (s, 1 H), 7.63 (s, 1 H), 7.25 (d, J=3.6 Hz, 1 H), 7.39 (s, 1 H), 7.01 (d, J=3.6 Hz, 1 H), 3.60 (s, 2 H), 2.55-2.44 (m, 8 H), 2.24 (s, 3 H).

(Exact m/z 527.16, m/z 528.96)

Example 13

Synthesis of 4-chloro-N-(4-(2-oxo-2,3-dihydro-1H-thieno[3,4-b][1,4]diazepine-4-yl)phenyl)benzamide

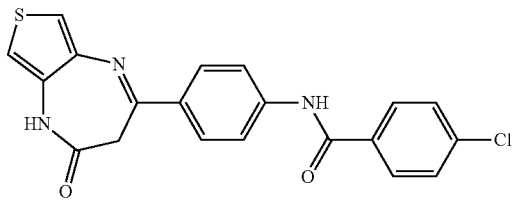 [SMILES: O=C1CC(c2ccc(NC(=O)c3ccc(Cl)cc3)cc2)=Nc2cscc2N1]

4-chlorobenzoic acid (9 mg, 0.058 mmol), 1-[bis(dimethylamino)methylene]-1H-1,2,3-triazolo[4,5-b]pyridinium 3-oxid hexafluorophosphate (33 mg, 0.087 mmol), and TEA (11 mg, 0.116 mmol) were dissolved in DMF (0.48 ml), the solution was stirred at 45° C. for 30 minutes, the compound F (15 mg, 0.058 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 4-chloro-N-(4-(2-oxo-2,3-dihydro-1H-thieno[3,4-b][1,4]diazepine-4-yl)phenyl)benzamide (9 mg, 39%).

$^1$H NMR (400 MHz, DMSO-d$_6$) δ 10.58 (s, 1 H), 10.50 (s, 1 H), 8.04-8.02 (m, 2 H), 8.01 (t, J=1.9 Hz, 2 H), 7.94 (d, J=9.0 Hz, 2 H), 7.63 (dd, J=7.2, 1.5 Hz, 2 H), 7.50 (d, J=3.7 Hz, 1 H), 7.02 (dd, J=3.5, 1.9 Hz, 1 H), 3.60 (s, 2 H).

(Exact mass 395.05, m/z 395.86)

Example 14

Synthesis of 2-(1H-indol-3-yl)-N-(4-(2-oxo-2,3-dihydro-1H-thieno[3,4-b][1,4]diazepine-4-yl)phenyl) acetamide

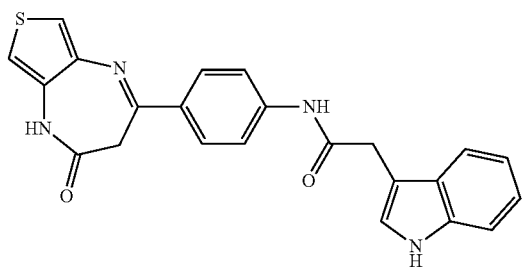 [SMILES: O=C(Cc1c[nH]c2ccccc12)Nc1ccc(C2=Nc3cscc3NC(=O)C2)cc1]

2-(1H-indol-3-yl)acetic acid (13 mg, 0.077 mmol), 1-[bis(dimethylamino)methylene]-1H-1,2,3-triazolo[4,5-b]pyridinium 3-oxid hexafluorophosphate (43 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 2-(1H-indol-3-yl)-N-(4-(2-oxo-2,3-dihydro-1H-thieno[3,4-b][1,4]diazepine-4-yl)phenyl)acetamide (17 mg, 53%).

$^1$H NMR (400 MHz, DMSO-d$_6$) δ 10.94 (1 H, s), 10.46 (1 H, s), 10.39 (1 H, s), 7.97 (2 H, d, J=8.9 Hz), 7.75 (2 H, d, J=8.9 Hz), 7.61 (1 H, d, J=7.9 Hz), 7.47 (1 H, d, J=3.7 Hz), 7.35 (1 H, d, J=8.0 Hz), 7.27 (1 H, d, J=2.3 Hz), 7.09-7.05 (1 H, m), 7.01-6.98 (2 H, m), 3.77 (2 H, s), 3.56 (2 H, s)

(Exact mass 414.12, m/z 415.12)

Example 15

Synthesis of 2-(2-cyanophenylthio)-N-(4-(2-oxo-2,3-dihydro-1H-thieno[3,4-b][1,4]diazepine-4-yl)phenyl)benzamide

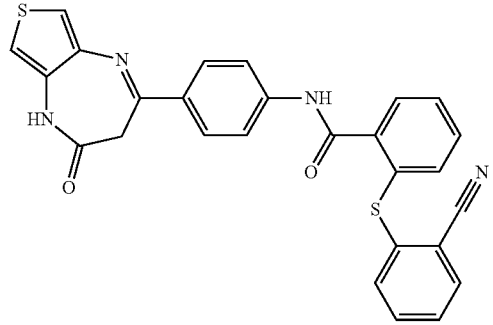 [SMILES: N#Cc1ccccc1Sc1ccccc1C(=O)Nc1ccc(C2=Nc3cscc3NC(=O)C2)cc1]

2-(2-cyanophenylthio)benzoic acid (19.6 mg, 0.077 mmol), 1-[bis(dimethylamino)methylene]-1H-1,2,3-triazolo

[4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 2-(2-cyanophenylthio)-N-(4-(2-oxo-2,3-dihydro-1H-thieno[3,4-b][1,4]diazepine-4-yl)phenyl)benzamide (7 mg, 18%).

$^1$H NMR (400 MHz, DMSO-d$_6$) δ 7.90 (1 H, d, J=1.2 Hz), 7.88 (1 H, d, J=1.1 Hz), 7.73-7.66 (4 H, m), 7.52-7.34 (7 H, m), 7.25-7.22 (1 H, m), 3.06 (2 H, q, J=7.1 Hz).

(Exact mass 494.09, m/z=494.71)

Example 16

Synthesis of 2-(biphenyl-4-yl)-N-(4-(2-oxo-2,3-dihydro-1H-thieno[3,4-b][1,4]diazebine-4-yl)phenyl) acetamide

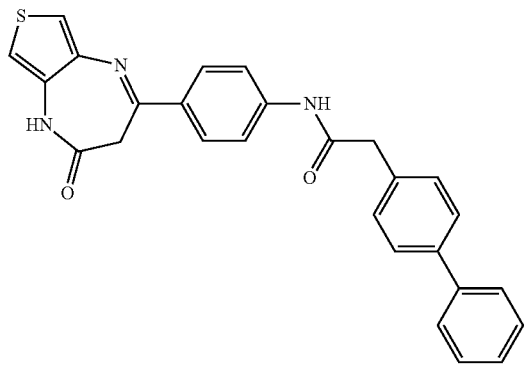 [SMILES: O=C(Cc1ccc(-c2ccccc2)cc1)Nc1ccc(C2=Nc3cscc3NC(=O)C2)cc1]

2-(biphenyl-4-yl)acetic acid (16.3 mg, 0.077 mmol), 1-[bis(dimethylamino)methylene]-1H-1,2,3-triazolo[4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 5p (26 mg, 74%).

$^1$H NMR (400 MHz, DMSO-d6) δ 10.48 (2 H, d, J=7.3 Hz), 7.99 (1 H, d, J=8.9 Hz), 7.75 (1 H, d, J=8.9 Hz), 7.68-7.60 (4 H, m), 7.59 (1 H, t, J=2.0 Hz), 7.51 (1 H, t, J=2.2 Hz), 7.48 (1 H, d, J=3.6 Hz), 7.47-7.41 (3 H, m), 7.38-7.30 (2 H, m), 7.00 (1 H, d, J=3.7 Hz), 3.72 (2 H, dd, J=14.4, 6.7 Hz), 3.57 (2 H, s).

(Exact mass 451.14, m/z 452.21)

Example 17

Synthesis of 3,5-dimethyl-N-(4-(2-oxo-2,3-dihydro-1H-thieno[3,4-b][1,4]diazepine-4-yl)phenyl)benzamide

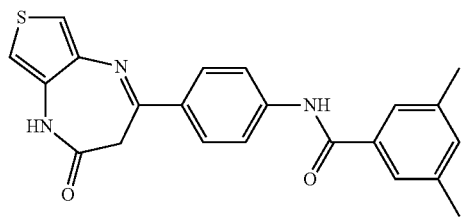 [SMILES: Cc1cc(C)cc(C(=O)Nc2ccc(C3=Nc4cscc4NC(=O)C3)cc2)c1]

3,5-dimethylbenzoic acid (8 mg, 0.058 mmol), 1-[bis(dimethylamino)methylene]-1H-1,2,3-triazolo[4,5-b]pyridinium 3-oxid hexafluorophosphate) (33 mg, 0.087 mmol), and TEA (11 mg, 0.116 mmol) were dissolved in DMF (0.48 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 3,5-dimethyl-N-(4-(2-oxo-2,3-dihydro-1H-thieno[3,4-b][1,4]diazepine-4-yl)phenyl)benzamide (9 mg, 39%).

$^1$H NMR (400 MHz, DMSO-d$_6$) δ 10.49 (s, 1 H), 10.43 (s, 1 H), 8.03 (d, J=8.9 Hz, 2 H), 7.94 (d, J=8.9 Hz, 2 H), 7.59 (s, 2 H), 7.50 (d, J=3.7 Hz, 1 H), 7.24 (s, 1 H), 7.01 (d, J=3.7 Hz, 1 H), 3.60 (s, 2 H), 2.37 (s, 6 H).

(Exact mass 389.12, m/z 389.47)

Example 18

Synthesis of 4-chloro-N-(3-(2-oxo-2,3-dihydro-1H-thieno[3,4-b][1,4]diazepine-4-yl)phenyl)-3-(trifluoromethyl)benzamide

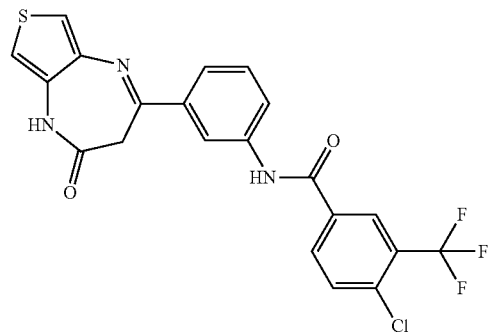 [SMILES: O=C1CC(c2cccc(NC(=O)c3ccc(Cl)c(C(F)(F)F)c3)c2)=Nc2cscc2N1]

4-chloro-3-(trifluoromethyl)benzoic acid (9.6 mg, 0.042 mmol), 1-[bis(dimethylamino)methylene]-1H-1,2,3-triazolo[4,5-b]pyridinium 3-oxid hexafluorophosphate (22.2 mg, 0.059 mmol), and TEA (7.2 mg, 0.078 mmol) were dissolved in DMF (0.2 ml), the solution was stirred at 45° C. for 30 minutes, the compound F (10 mg, 0.039 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 4-chloro-N-(3-(2-oxo-2,3-dihydro-1H-thieno[3,4-b][1,4]diazepine-4-yl)phenyl)-3-(trifluoromethyl)benzamide (13.4 mg, 74%).

$^1$H NMR (400 MHz, DMSO-d$_6$) δ 10.73 (1 H, s), 10.53 (1 H, s), 8.44 (1 H, d, J=2.0 Hz), 8.41 (1 H, t, J=1.8 Hz), 8.30 (1 H, dd, J=8.4, 2.0 Hz), 8.03 (1 H, dd, J=7.2, 1.2 Hz), 7.94 (1 H, d, J=8.4 Hz), 7.78 (1 H, d, J=8.4 Hz), 7.56-7.52 (2 H, m), 7.03 (1 H, d, J=3.6 Hz), 3.61 (2 H, s)

(Exact mass 463.04, m/z 464.0418)

Example 19

Synthesis of 3-(4-methyl-1H-imidazol-1-yl)-N-(3-(2-oxo-2,3-dihydro-1H-thieno[3,4-b][1,4]diazepine-4-yl)phenyl)-5-(trifluoromethyl)benzamide

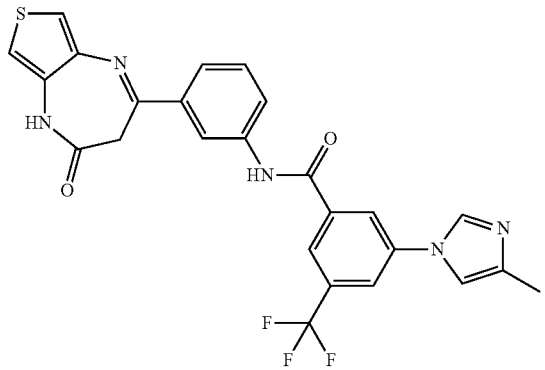 [SMILES: Cc1cn(-c2cc(C(=O)Nc3cccc(C4=Nc5cscc5NC(=O)C4)c3)cc(C(F)(F)F)c2)cn1]

3-(4-methyl-1H-imidazol-1-yl)-5-(trifluoromethyl)benzoic acid (12 mg, 0.0436 mmol), 1-[bis(dimethylamino)methylene]-1H-1,2,3-triazolo[4,5-b]pyridinium 3-oxid hexafluorophosphate (22.6 mg, 0.059 mmol), and TEA (7.2 mg, 0.078 mmol) were dissolved in DMF (0.2 ml), the solution was stirred at 45° C. for 30 minutes, the compound F (10.2 mg, 0.039 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was crystallized to obtain a target compound 3-(4-methyl-1H-imidazol-1-yl)-N-(3-(2-oxo-2,3-dihydro-1H-thieno[3,4-b][1,4]diazepine-4-yl)phenyl)-5-(trifluoromethyl)benzamide (15.6 mg, 78%).

$^1$H NMR (400 MHz, DMSO-d$_6$) δ 10.71 (1 H, s), 10.53 (1 H, s), 8.49 (1 H, s), 8.43-8.42 (2 H, m), 8.26 (1 H, s), 8.22 (1 H, s), 8.06 (1 H, dd, J=8.2, 1.4 Hz), 7.79 (1 H, d, J=8.0 Hz), 7.73 (1 H, s), 7.58-7.54 (2 H, m), 7.04 (1 H, d, J=4.0 Hz), 3.61 (2 H, s), 2.20 (3 H, s)

(Exact mass 509.11, m/z 510 10.1186)

Example 20

Synthesis of 3-morpholino-N-(3-(2-oxo-2,3-dihydro-1H-thieno[3,4-b][1,4]diazepine-4-yl)phenyl)-5-(trifluoromethyl)benzamide

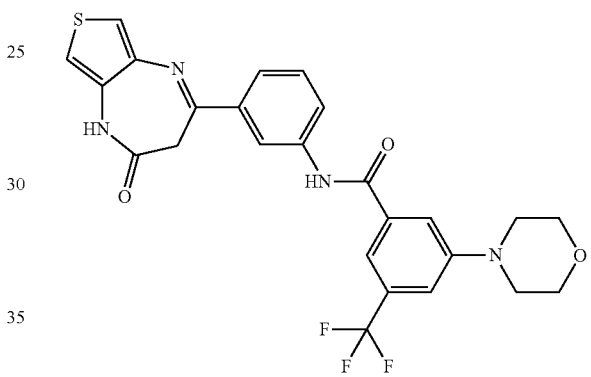

3-morpholino-5-(trifluoromethyl)benzoic acid (12 mg, 0.043 mmol), 1-[bis(dimethylamino)methylene]-1H-1,2,3-triazolo[4,5-b]pyridinium 3-oxid hexafluorophosphate (22.6 mg, 0.059 mmol), and TEA (8 mg, 0.079 mmol) were dissolved in DMF (0.2 ml), the solution was stirred at 45° C. for 30 minutes, the compound F (10 mg, 0.039 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 3-morpholino-N-(3-(2-oxo-2,3-dihydro-1H-thieno[3,4-b][1,4]diazepine-4-yl)phenyl)-5-(trifluoromethyl)benzamide (12.6 mg, 62%).

$^1$H NMR (400 MHz, DMSO-d$_6$) δ 10.56 (1 H, s), 10.53 (1 H, s), 8.40 (1 H, s), 8.02 (1 H, d, J=9.2 Hz), 7.77-7.75 (2 H, m), 7.70 (1 H, s), 7.55-7.51 (2 H, s), 7.41 (1 H, s), 7.03 (1 H, d, J=3.6 Hz), 3.78 (4 H, t, J=4.6 Hz), 3.61 (2 H, s)

(Exact mass 514.13, m/z 515.1331)

Example 21

Synthesis of 4-morpholino-N-(3-(2-oxo-2,3-dihydro-1H-thieno[3,4-b][1,4] diazepine-4-yl)phenyl)-3-(trifluoromethyl)benzamide

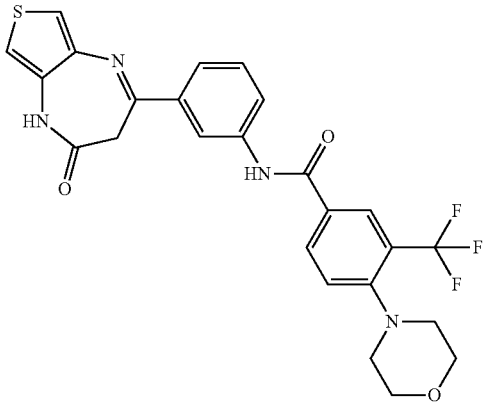 [SMILES: O=C1CC(c2cccc(NC(=O)c3ccc(N4CCOCC4)c(C(F)(F)F)c3)c2)=Nc2cscc2N1]

4-morpholino-3-(trifluoromethyl)benzoic acid (12 mg, 0.043 mmol), 1-[bis(dimethylamino)methylene]-1H-1,2,3-triazolo[4,5-b]pyridinium 3-oxid hexafluorophosphate (22.6 mg, 0.059 mmol), and TEA (8 mg, 0.079 mmol) were dissolved in DMF (0.2 ml), the solution was stirred at 45° C. for 30 minutes, the compound F (10 mg, 0.039 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 4-morpholino-N-(3-(2-oxo-2,3-dihydro-1H-thieno[3,4-b][1,4]diazepine-4-yl)phenyl)-3-(trifluoromethyl)benzamide (5 mg).

$^1$H NMR (400 MHz, DMSO-$d_6$) δ 10.57 (1 H, s), 10.52 (1 H, s), 8.42 (1 H, t, J=1.8 Hz), 8.30-8.27 (2 H, m), 8.02 (1 H, dd, J=8.0, 1.2 Hz), 7.76 (1 H, d, J=7.6 Hz), 7.66 (1 H, d, J=8.4 Hz), 7.54-7.50 (2 H, m), 7.03 (1 H, d, J=3.6 Hz), 3.74 (4 H, t, J=4.4 Hz), 3.61 (2 H, s), 2.97 (4 H, t, J=4.4 Hz)

(Exact mass 514.13, m/z 515.1335)

Example 22

Synthesis of N-(3-(2-oxo-2,3-dihydro-1H-thieno[3,4-b][1,4]diazepine-4-yl)phenyl)biphenyl-4-carboxamide

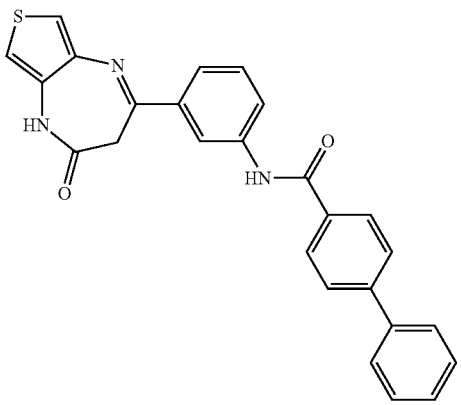 [SMILES: O=C1CC(c2cccc(NC(=O)c3ccc(-c4ccccc4)cc3)c2)=Nc2cscc2N1]

Biphenyl-4-carboxylic acid (6.2 mg, 0.031 mmol), 1-[bis(dimethylamino)methylene]-1H-1,2,3-triazolo[4,5-b]pyridinium 3-oxid hexafluorophosphate (16 mg, 0.042 mmol), and TEA (5.7 mg, 0.056 mmol) were dissolved in DMF (0.2 ml), the solution was stirred at 45° C. for 30 minutes, the compound F (10 mg, 0.039 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(3-(2-oxo-2,3-dihydro-1H-thieno[3,4-b][1,4]diazepine-4-yl)phenyl)biphenyl-4-carboxamide (2.5 mg, 14%).

$^1$H NMR (400 MHz, DMSO-$d_6$) δ 10.54 (1 H, s), 10.52 (1 H, s), 8.48 (1 H, s), 8.11 (2 H, d, J=8.4 Hz), 8.04 (1 H, d, J=7.2 Hz), 7.86 (2 H, d, J=8.8 Hz), 7.79-7.75 (3 H, m), 7.55-7.52 (4 H, m), 7.43 (1 H, d, J=7.2 Hz), 7.04 (1 H, d, J=4.0 Hz), 3.62 (2 H, s)

(Exact mass 437.12, m/z 438.1255)

Example 23

Synthesis of N-(3-(2-oxo-2,3-dihydro-1H-thieno[3,4-b][1,4]diazepine-4-yl)phenyl)biphenyl-2-carboxamide

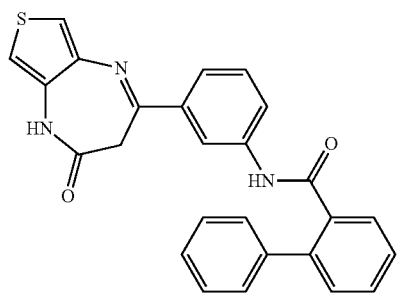 [SMILES: O=C1CC(c2cccc(NC(=O)c3ccccc3-c3ccccc3)c2)=Nc2cscc2N1]

Biphenyl-2-carboxylic acid (6 mg, 0.030 mmol), 1-[bis(dimethylamino)methylene]-1H-1,2,3-triazolo[4,5-b]pyridinium 3-oxid hexafluorophosphate (15 mg, 0.040 mmol), and TEA (5.5 mg, 0.054 mmol) were dissolved in DMF (0.2 ml), the solution was stirred at 45° C. for 30 minutes, the compound F (7 mg, 0.027 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(3-(2-oxo-2,3-dihydro-1H-thieno[3,4-b][1,4]diazepine-4-yl)phenyl)biphenyl-2-carboxamide (6.5 mg, 55%).

$^1$H NMR (400 MHz, DMSO-$d_6$) δ 10.49 (1 H, s), 10.43 (1 H, s), 8.25 (1 H, s), 7.68 (2 H, d, J=8.0 Hz), 7.61-7.57 (2 H, m), 7.52 (1 H, d, J=3.6 Hz), 7.49-7.41 (4 H, m), 7.40-7.36 (3 H, m), 7.30 (1 H, t, J=7.2 Hz), 7.01 (1 H, d, J=3.6 Hz), 3.55 (2 H, s)

(Exact mass 437.12, m/z 438.1258)

Example 24

Synthesis of N-(3-(2-oxo-2,3-dihydro-1H-thieno[3,4-b][1,4]diazepine-4-yl)phenyl)-1-phenyl-5-(trifluoromethyl)-1H-pyrazole-4-carboxamide

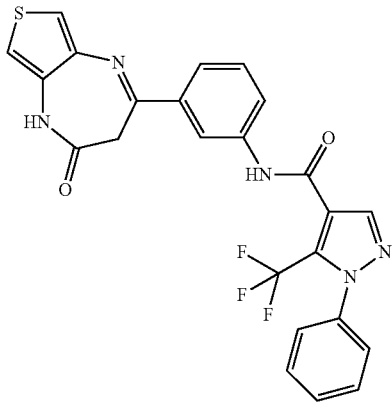 [SMILES: O=C1CC(c2cccc(NC(=O)c3cnn(-c4ccccc4)c3C(F)(F)F)c2)=Nc2cscc2N1]

1-phenyl-5-(trifluoromethyl)-1H-pyrazole-4-carboxylic acid (7.1 mg, 0.028 mmol), 1-[bis(dimethylamino)methylene]-1H-1,2,3-triazolo[4,5-b]pyridinium 3-oxid hexafluorophosphate (16 mg, 0.042 mmol), and TEA (5.7 mg, 0.056 mmol) were dissolved in DMF (0.2 ml), the solution was stirred at 45° C. for 30 minutes, the compound F (7.1 mg, 0.028 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(3-(2-oxo-2,3-dihydro-1H-thieno[3,4-b][1,4]diazepine-4-yl)phenyl)-1-phenyl-5-(trifluoromethyl)-1H-pyrazole-4-carboxamide (12 mg, 86%).

$^1$H NMR (400 MHz, DMSO-$d_6$) δ 10.74 (1 H, s), 10.54 (1 H, s), 8.38 (1 H, s), 8.36 (1 H, s), 7.94 (1 H, d, J=8.4 Hz), 7.76 (1 H, d, J=8.4 Hz), 7.63-7.61 (4 H, m), 7.56-7.50 (3 H, m), 7.04 (1 H, d, J=4.0 Hz), 3.61 (2 H, s)

(Exact mass 459.10, m/z 496.102)

Example 25

Synthesis of 1-acetyl-N-(3-(2-oxo-2,3-dihydro-1H-thieno[3,4-b][1,4]diazepine-4-yl)phenyl)piperidine-4-carboxamide

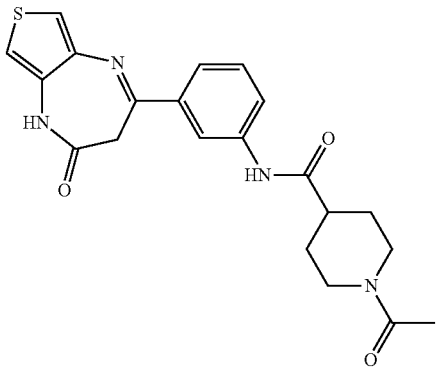 [SMILES: CC(=O)N1CCC(C(=O)Nc2cccc(C3=Nc4cscc4NC(=O)C3)c2)CC1]

1-acetylpiperidine-4-carboxylic acid (5.1 mg, 0.03 mmol), 1-[bis(dimethylamino)methylene]-1H-1,2,3-triazolo[4,5-b]pyridinium 3-oxid hexafluorophosphate (15.5 mg, 0.041 mmol), and TEA (5.5 mg, 0.054 mmol) were dissolved in DMF (0.2 ml), the solution was stirred at 45° C. for 30 minutes, the compound F (7 mg, 0.027 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 1-acetyl-N-(3-(2-oxo-2,3-dihydro-1H-thieno[3,4-b][1,4]diazepine-4-yl)phenyl)piperidine-4-carboxamide (8.5 mg, 76%).

$^1$H NMR (400 MHz, DMSO-$d_6$) δ 10.52 (1 H, s), 10.15 (1 H, s), 8.26 (1 H, t, J=1.6 Hz), 7.83 (1 H, d, J=8.0 Hz), 7.67 (1 H, d, J=8.4 Hz), 7.53 (1 H, d, J=3.6 Hz), 7.44 (1 H, t, J=8.0 Hz), 7.02 (1 H, d, J=3.6 Hz), 3.89-3.86 (1 H, m), 3.55 (2 H, s), 3.11-3.04 (1 H, m), 2.63-2.56 (3 H, m), 2.04 (3 H, s), 1.64-1.54 (2 H, m), 1.46-1.2 (2 H, m)

(Exact mass 410.14, m/z 411.1473)

Example 26

Synthesis of 2,2-bis(4-chlorophenyl)-N-(3-(2-oxo-2,3-dihydro-1H-thieno[3,4-b][1,4]diazepine-4-yl)phenyl)acetamide

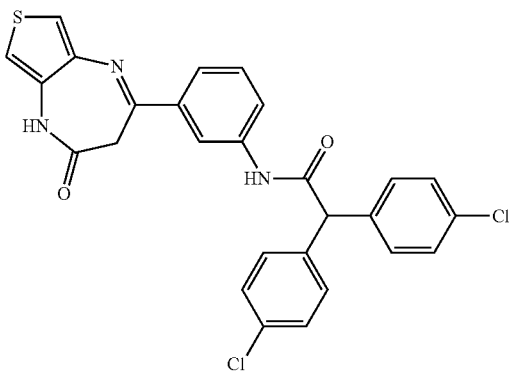 [SMILES: O=C1CC(c2cccc(NC(=O)C(c3ccc(Cl)cc3)c3ccc(Cl)cc3)c2)=Nc2cscc2N1]

2,2-bis(4-chlorophenyl)acetic acid (8.2 mg, 0.029 mmol), 1-[bis(dimethylamino)methylene]-1H-1,2,3-triazolo[4,5-b]pyridinium 3-oxid hexafluorophosphate (15 mg, 0.040 mmol), and TEA (5.3 mg, 0.052 mmol) were dissolved in DMF (0.2 ml), the solution was stirred at 45° C. for 30 minutes, the compound F (6.8 mg, 0.026 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 2,2-bis(4-chlorophenyl)-N-(3-(2-oxo-2,3-dihydro-1H-thieno[3,4-b][1,4]diazepine-4-yl)phenyl)acetamide (4 mg, 29%).

$^1$H NMR (400 MHz, DMSO-$d_6$) δ 10.69 (1 H, s), 10.52 (1 H, s), 8.23 (1 H, t, J=1.8 Hz), 7.83 (1 H, dd, J=8.0, 1.2

Hz), 7.70 (1 H, d, J=8.4 Hz), 7.52 (1 H, d, J=3.6 Hz), 7.44-7.41 (5H, m), 7.38-7.36 (4 H, m), 7.02 (1 H, d, J=3.6 Hz), 3.56 (2 H, s)

(Exact mass 519.06 m/z 520.0677)

Example 27

Synthesis of N-(3-(2-oxo-2,3-dihydro-1H-thieno[3,4-b][1,4]diazepine-4-yl)phenyl)isonicotinamide

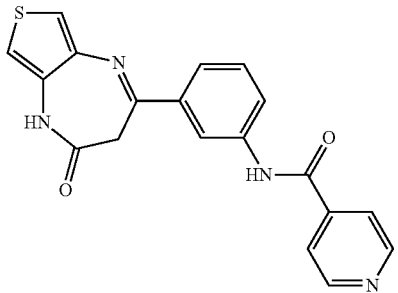 [SMILES: O=C1CC(c2cccc(NC(=O)c3ccncc3)c2)=Nc2cscc2N1]

Isonicotinic acid (9.4 mg, 0.077 mmol), 1-[bis(dimethylamino)methylene]-1H-1,2,3-triazolo[4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(3-(2-oxo-2,3-dihydro-1H-thieno[3,4-b][1,4]diazepine-4-yl)phenyl) isonicotinamide (8 mg, 28%).

$^1$H NMR (400 MHz, DMSO-d$_6$) δ 12.43 (s, 1 H), 10.72 (s, 1 H), 8.79 (d, J=5.5 Hz, 2 H), 8.29 (dd, J=4.4, 2.6 Hz, 2 H), 8.21 (d, J=8.1 Hz, 1 H), 7.86 (dd, J=4.4, 1.6 Hz, 2 H), 7.74 (dd, J=6.6, 1.6 Hz, 1 H), 7.59 (t, J=7.9 Hz, 1 H), 7.05 (d, J=3.3 Hz, 1 H), 3.51 (d, J=0.8 Hz, 2 H).

(Exact mass 362.08, m/z 362.41)

Example 28

Synthesis of N-(3-(2-oxo-2,3-dihydro-1H-thieno[3,4-b][1,4]diazepine-4-yl)phenyl)pyrazine-2-carboxamide

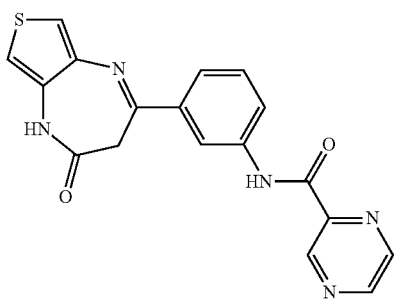 [SMILES: O=C1CC(c2cccc(NC(=O)c3cnccn3)c2)=Nc2cscc2N1]

Pyrazine-2-carboxylic acid (13 mg, 0.077 mmol), 1-[bis(dimethylamino)methylene]-1H-1,2,3-triazolo[4,5-b]pyridinium 3-oxid hexafluorophosphate (43 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(3-(2-oxo-2,3-dihydro-1H-thieno[3,4-b][1,4]diazepine-4-yl)phenyl)pyrazine-2-carboxamide (29 mg, 99%).

$^1$H NMR (400 MHz, DMSO-d$_6$) δ 10.97 (1 H, s), 10.53 (1 H, s), 9.33 (1 H, d, J=1.5 Hz), 8.95 (1 H, d, J=2.5 Hz), 8.84 (1 H, dd, J=2.5, 1.5 Hz), 8.63 (1 H, s), 8.07 (1 H, dd, J=8.1, 1.3 Hz), 7.80 (1 H, d, J=8.5 Hz), 7.57-7.50 (2 H, m), 7.03 (1 H, d, J=3.7 Hz), 3.62 (2 H, s)

(Exact mass 363.08, m/z 364.08)

Example 29

Synthesis of 3-(4-methylpiperazine-1-yl)-N-(3-(2-oxo-2,3-dihydro-1H-thieno[3,4-b][1,4]diazepine-4-yl)phenyl)-5-(trifluoromethyl)benzamide

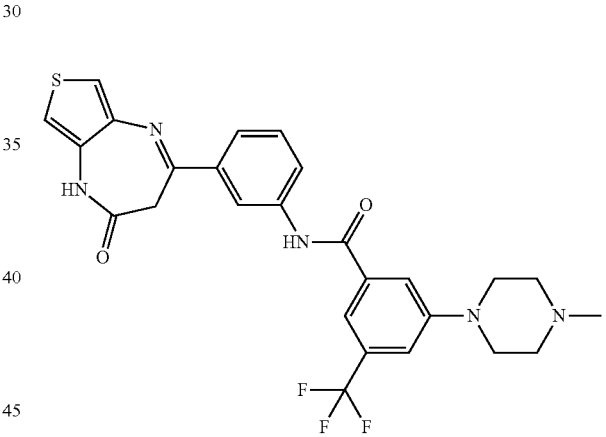

3-(4-methylpiperazine-1-yl)-5-(trifluoromethyl)benzoic acid (33.6 mg, 0.116 mmol), 1-[bis(dimethylamino)methylene]-1H-1,2,3-triazolo[4,5-b]pyridinium 3-oxid hexafluorophosphate (66.1 mg, 0.17 mmol) and TEA (23.6 mg, 0.23 mmol) were dissolved in DMF (0.96 ml), the solution was stirred at 45° C. for 30 minutes, the compound F (30 mg, 0.116 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 3-(4-methylpiperazine-1-yl)-N-(3-(2-oxo-2,3-dihydro-1H-thieno[3,4-b][1,4]diazepine-4-yl)phenyl)-5-(trifluoromethyl)benzamide (39 mg, 63%).

$^1$H NMR (400 MHz, DMSO-d$_6$) δ 10.55 (s, 1 H), 10.53 (s, 1 H), 8.40 (t, J=3.6 Hz, 1 H), 8.00 (d, d, J=1.2, 1.2 Hz, 1 H), 7.73 (d, J=2.4 Hz, 2 H), 7.65 (s, 1 H), 7.54-7.50 (t, s,

J=7.6 Hz, 2 H), 7.38 (s, 1 H), 7.01 (d, J=4 Hz, 1 H), 3.61 (s, 2 H), 2.55-2.45 (m, 8 H), 2.23 (s, 3 H)

(Exact mass 527.16, m/z 528.99)

Example 30

Synthesis of 4-chloro-N-(3-(2-oxo-2,3-dihydro-1H-thieno[3,4-b][1,4]diazepine-4-yl)phenyl)benzamide

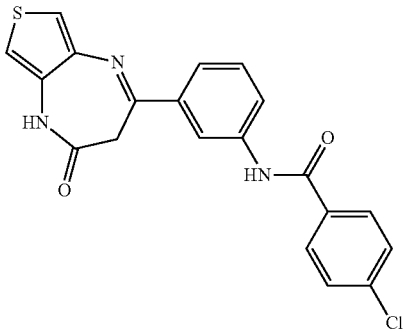 [SMILES: O=C1CC(c2cccc(NC(=O)c3ccc(Cl)cc3)c2)=Nc2cscc2N1]

4-chlorobenzoic acid (7.1 mg, 0.045 mmol), 1-[bis(dimethylamino)methylene]-1H-1,2,3-triazolo[4,5-b]pyridinium 3-oxid hexafluorophosphate (23.3 mg, 0.061 mmol), and TEA (8.3 mg, 0.082 mmol) were dissolved in DMF (0.2 ml), the solution was stirred at 45° C. for 30 minutes, the compound F (10.5 mg, 0.041 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 4-chloro-N-(3-(2-oxo-2,3-dihydro-1H-thieno[3,4-b][1,4]diazepine-4-yl)phenyl)benzamide (5 mg).

$^1$H NMR (400 MHz, DMSO-$d_6$) δ 10.54 (2 H, s), 8.43 (1 H, t, J=1.6 Hz), 8.04-8.00 (3 H, m), 7.75 (1 H, d, J=8.0 Hz), 7.63 (2 H, d, J=8.8 Hz), 7.55-7.49 (2 H, m), 7.03 (1 H, d, J=3.6 Hz), 3.61 (2 H, s)

(Exact mass 395.05, m/z 396.0547)

Example 31

Synthesis of 2-(1H-indol-3-yl)-N-(3-(2-oxo-2,3-dihydro-1H-thieno[3,4-b][1,4]diazepine-4-yl)phenyl) acetamide

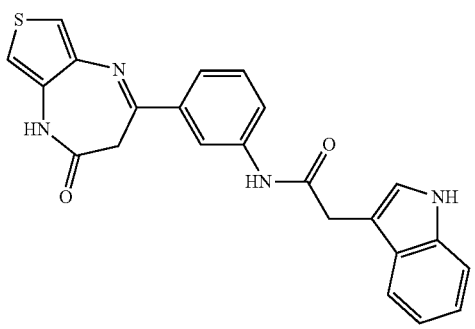 [SMILES: O=C(Cc1c[nH]c2ccccc12)Nc1cccc(C2=Nc3cscc3NC(=O)C2)c1]

2-(1H-indol-3-yl)acetic acid (13 mg, 0.077 mmol), 1-[bis (dimethylamino)methylene]-1H-1,2,3-triazolo[4,5-b]pyridinium 3-oxid hexafluorophosphate (43 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 2-(1H-indol-3-yl)-N-(3-(2-oxo-2,3-dihydro-1H-thieno[3,4-b][1,4]diazepine-4-yl)phenyl)acetamide (30 mg, 93%).

$^1$H NMR (400 MHz, DMSO-$d_6$) δ 10.93 (1 H, s), 10.51 (1 H, s), 10.33 (1 H, s), 8.25 (1 H, t, J=1.8 Hz), 7.88-7.82 (1 H, m), 7.63 (1 H, dd, J=16.6, 8.1 Hz), 7.52 (1 H, d, J=3.7 Hz), 7.43 (1 H, t, J=8.0 Hz), 7.35 (1 H, dt, J=8.1, 0.9 Hz), 7.27 (1 H, d, J=2.3 Hz), 7.07 (1 H, ddd, J=8.1, 7.0, 1.2 Hz), 7.01 (1 H, dd, J=5.1, 2.4 Hz), 6.99-6.96 (1 H, m), 3.75 (2 H, s), 3.56 (2 H, s).

(Exact mass 414.12, m/z 415.12)

Example 32

Synthesis of 2-(2-cyanophenylthio)-N-(3-(2-oxo-2,3-dihydro-1H-thieno[3,4-b][1,4]diazepine-4-yl)phenyl)benzamide

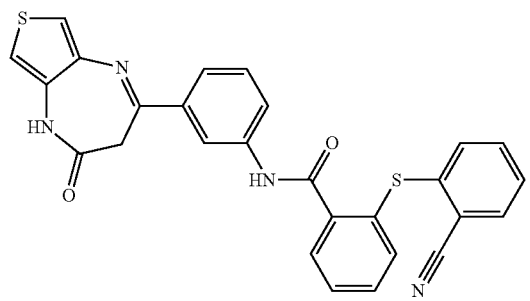 [SMILES: N#Cc1ccccc1Sc1ccccc1C(=O)Nc1cccc(C2=Nc3cscc3NC(=O)C2)c1]

2-(2-cyanophenylthio)benzoic acid (19.6 mg, 0.077 mmol), 1-[bis(dimethylamino)methylene]-1H-1,2,3-triazolo [4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 2-(2-cyanophenylthio)-N-(3-(2-oxo-2,3-dihydro-1H-thieno[3,4-b][1,4] diazepine-4-yl)phenyl)benzamide (25 mg, 65%).

$^1$H NMR (400 MHz, DMSO-$d_6$) δ 10.72 (1 H, s), 10.53 (1 H, s), 8.40 (1 H, s), 7.94-7.88 (1 H, m), 7.77-7.75 (1 H, m), 7.70-7.66 (2 H, m), 7.55 (1 H, d, J=3.7 Hz), 7.52-7.48 (4 H, m), 7.44 (2 H, dd, J=7.9, 2.9 Hz), 7.20-7.16 (1 H, m), 7.03 (1 H, d, J=3.7 Hz), 3.59 (2 H, s)

(Exact mass 494.09, m/z 495.09)

Example 33

Synthesis of 2-(biphenyl-4-yl)-N-(3-(2-oxo-2,3-dihydro-1H-thieno[3,4-b][1,4]diazepine-4-yl)phenyl)acetamide

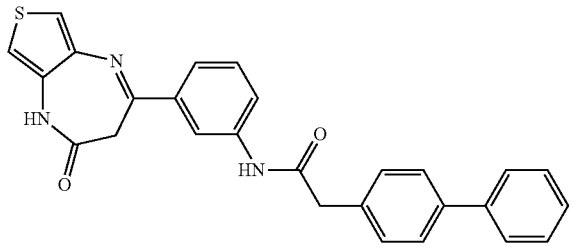 [SMILES: O=C(Cc1ccc(-c2ccccc2)cc1)Nc1cccc(C2=Nc3cscc3NC(=O)C2)c1]

2-(biphenyl-4-yl)acetic acid (16.3 mg, 0.077 mmol), 1-[bis(dimethylamino)methylene]-1H-1,2,3-triazolo[4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 2-(biphenyl-4-yl)-N-(3-(2-oxo-2,3-dihydro-1H-thieno[3,4-b][1,4] diazepine-4-yl)phenyl)acetamide (31 mg, 89%).

$^1$H NMR (400 MHz, DMSO-d$_6$) δ 10.52 (1 H, s), 10.44 (1 H, s), 8.26 (1 H, t, J=1.8 Hz), 7.85 (1 H, dd, J=8.1, 1.2 Hz), 7.66 (1 H, d, J=1.4 Hz), 7.64 (2 H, s), 7.62 (1 H, d, J=1.8 Hz), 7.52 (1 H, d, J=3.7 Hz), 7.47 (1 H, d, J=1.7 Hz), 7.46 (2 H, d, J=1.3 Hz), 7.43 (2 H, d, J=2.0 Hz), 7.38-7.36 (1 H, m), 7.35 (1 H, d, J=1.8 Hz), 7.02 (1 H, d, J=3.7 Hz), 3.71 (2 H, d, J=4.4 Hz), 3.57 (2 H, s)

(Exact mass 451.14, m/z 452.14)

Example 34

Synthesis of 3,5-dimethyl-N-(3-(2-oxo-2,3-dihydro-1H-thieno[3,4-b][1,4]diazepine-4-yl)phenyl)benzamide

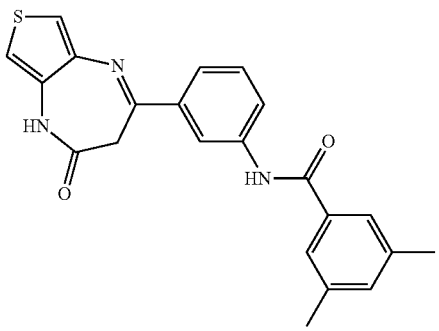 [SMILES: Cc1cc(C)cc(C(=O)Nc2cccc(C3=Nc4cscc4NC(=O)C3)c2)c1]

3,5-dimethylbenzoic acid (11 mg, 0.077 mmol), 1-[bis(dimethylamino)methylene]-1H-1,2,3-triazolo[4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 3,5-dimethyl-N-(3-(2-oxo-2,3-dihydro-1H-thieno[3,4-b][1,4] diazepine-4-yl)phenyl)benzamide (26 mg, 86%).

$^1$H NMR (400 MHz, DMSO-d$_6$) δ 10.54 (1 H, s), 10.38 (1 H, s), 8.43 (1 H, t, J=1.8 Hz), 8.05-8.00 (1 H, m), 7.75-7.72 (1 H, m), 7.62-7.47 (6H, m), 7.24 (2 H, d, J=5.9 Hz), 7.04 (2 H, dd, J=8.2, 3.5 Hz), 6.98-6.96 (1 H, m), 6.92-6.89 (1 H, m), 3.61 (2 H, s)

(Exact mass 389.12, m/z 390.12)

Example 35

Synthesis of 2-(2-fluorophenyl)-N-(3-(2-oxo-2,3-dihydro-1H-thieno[3,4-b][1,4]diazepine-4-yl)phenyl)acetamide

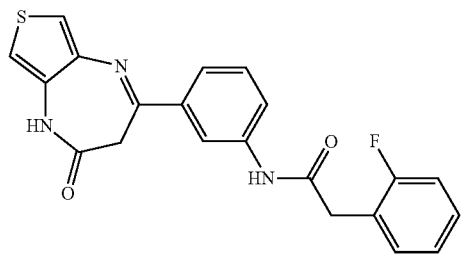 [SMILES: O=C(Cc1ccccc1F)Nc1cccc(C2=Nc3cscc3NC(=O)C2)c1]

2-(2-fluorophenyl)acetic acid (11 mg, 0.077 mmol), 1-[bis(dimethylamino)methylene]-1H-1,2,3-triazolo[4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 2-(2-fluorophenyl)-N-(3-(2-oxo-2,3-dihydro-1H-thieno[3,4-b][1,4] diazepine-4-yl)phenyl)acetamide (24 mg, 79%).

$^1$H NMR (400 MHz, DMSO-d$_6$) δ 10.52 (1 H, s), 10.45 (1 H, s), 8.29-8.26 (1 H, m), 7.81 (1 H, ddd, J=7.8, 1.8, 0.7 Hz), 7.68 (1 H, ddd, J=7.9, 1.8, 1.1 Hz), 7.52 (1 H, d, J=3.7 Hz), 7.46 (1 H, d, J=8.0 Hz), 7.41-7.39 (1 H, m), 7.32-7.29 (1 H, m), 7.19-7.17 (2 H, m), 7.02 (1 H, d, J=3.7 Hz), 3.76 (2 H, s), 3.57 (2 H, s)

(Exact mass 393.09, m/z 394.10)

Example 36

Synthesis of N-(3-(2-oxo-2,3-dihydro-1H-thieno[3,4-b][1,4]diazepine-4-yl)phenyl)quinoline-2-carboxamide

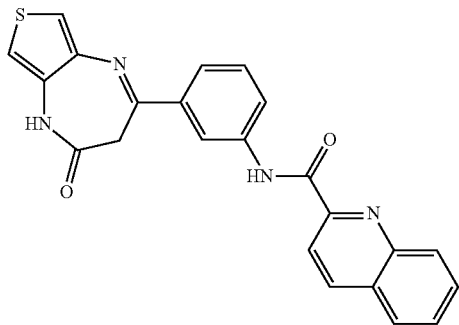 [SMILES: O=C1CC(c2cccc(NC(=O)c3ccc4ccccc4n3)c2)=Nc2cscc2N1]

Quinoline-2-carboxylic acid (13 mg, 0.077 mmol), 1-[bis(dimethylamino)methylene]-1H-1,2,3-triazolo[4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(3-(2-oxo-2,3-dihydro-1H-thieno[3,4-b][1,4]diazepine-4-yl)phenyl) quinoline-2-carboxamide (21 mg, 66%).

$^1$H NMR (400 MHz, DMSO-$d_6$) δ 10.98 (1 H, s), 10.55 (1 H, s), 8.64 (1 H, t, J=8.3 Hz), 8.55 (1 H, s), 8.48 (1 H, d, J=8.5 Hz), 8.27 (1 H, dd, J=11.3, 2.8 Hz), 8.14 (1 H, dd, J=15.4, 6.7 Hz), 8.04 (1 H, d, J=8.4 Hz), 7.97-7.91 (1 H, m), 7.85-7.74 (1 H, m), 7.71-7.65 (1 H, m), 7.63 (1 H, d, J=8.5 Hz), 7.60-7.53 (1 H, m), 7.04 (1 H, d, J=3.7 Hz), 3.66 (2 H, s).

(Exact mass 412.10, m/z 413.10)

Example 37

Synthesis of N-(3-(2-oxo-2,3-dihydro-1H-thieno[3,4-b][1,4]diazepine-4-yl)phenyl)quinoline-3-carboxamide

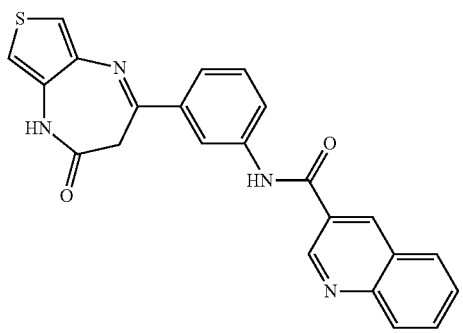 [SMILES: O=C1CC(c2cccc(NC(=O)c3cnc4ccccc4c3)c2)=Nc2cscc2N1]

Quinoline-3-carboxylic acid (13.3 mg, 0.077 mmol), 1-[bis(dimethylamino)methylene]-1H-1,2,3-triazolo[4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound N-(3-(2-oxo-2,3-dihydro-1H-thieno[3,4-b][1,4]diazepine-4-yl)phenyl) quinoline-3-carboxamide (28 mg, 88%).

$^1$H NMR (400 MHz, DMSO-$d_6$) δ 10.85 (1 H, s), 10.56 (1 H, s), 9.39 (1 H, dd, J=6.2, 2.2 Hz), 9.02 (1 H, d, J=2.0 Hz), 8.87 (1 H, d, J=2.2 Hz), 8.48 (1 H, t, J=2.0 Hz), 8.43 (1 H, d, J=2.1 Hz), 8.19-8.05 (1 H, m), 7.96-7.89 (1 H, m), 7.84 (1 H, ddd, J=8.5, 6.9, 1.4 Hz), 7.77-7.72 (1 H, m), 7.71-7.66 (1 H, m), 7.57-7.55 (1 H, m), 7.04 (1 H, d, J=3.7 Hz), 3.63 (2 H, s).

(Exact mass 412.10, m/z 413.10)

Example 38

Synthesis of (R)-6-hydroxy-2,5,7,8-tetramethyl-N-(3-(2-oxo-2,3-dihydro-1H-thieno[3,4-b][1,4]diazepine-4-yl)phenyl)chroman-2-carboxamide

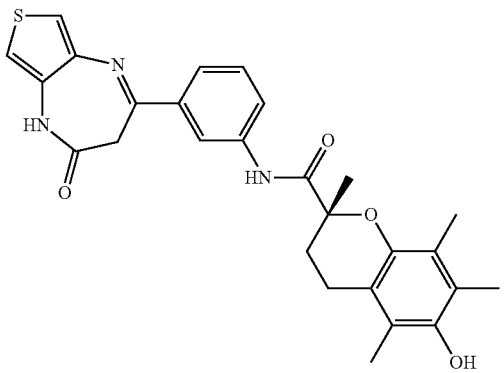 [SMILES: Cc1c(C)c2c(c(C)c1O)CC[C@](C)(C(=O)Nc1cccc(C3=Nc4cscc4NC(=O)C3)c1)O2]

(R)-6-hydroxy-2,5,7,8-tetramethylchroman-2-carboxylic acid (19 mg, 0.077 mmol), 1-[bis(dimethylamino)methylene]-1H-1,2,3-triazolo[4,5-b]pyridinium 3-oxid hexafluorophosphate (45 mg, 0.115 mmol), and TEA (56 mg, 0.154 mmol) were dissolved in DMF (0.64 ml), the solution was stirred at 45° C. for 30 minutes, the compound F (20 mg, 0.077 mmol) was then added, and the solution was stirred at 45° C. for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound (R)-6-hydroxy-2,5,7,8-tetramethyl-N-(3-(2-oxo-2,3-dihydro-1H-thieno[3,4-b][1,4]diazepine-4-yl)phenyl)chroman-2-carboxamide (34 mg, 90%).

¹H NMR (400 MHz, DMSO-d₆) δ 10.51 (1 H, s), 9.50 (1 H, s), 8.31 (1 H, t, J=1.9 Hz), 7.77 (1 H, ddd, J=8.2, 2.0, 0.8 Hz), 7.69 (1 H, ddd, J=7.8, 1.6, 1.0 Hz), 7.56-7.50 (3 H, m), 7.43 (1 H, t, J=8.0 Hz), 7.03 (1 H, dd, J=9.0, 3.5 Hz), 3.57 (2 H, s), 2.19 (3 H, d, J=3.0 Hz), 2.09-2.04 (7 H, m), 1.54-1.49 (5 H, m)

(Exact mass 489.17, m/z 490.18).

Example 39

Synthesis of 1-(4-chloro-3-(trifluoromethyl)phenyl)-3-(4-(2-oxo-2,3-dihydro-1H-thieno[3,4-b][1,4]diazepine-4-yl)phenyl)urea

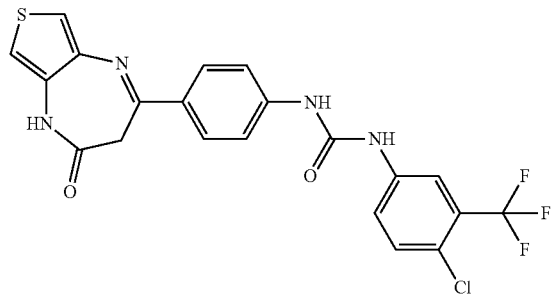 [SMILES: O=C1CC(c2ccc(NC(=O)Nc3ccc(Cl)c(C(F)(F)F)c3)cc2)=Nc2cscc2N1]

The compound F (10 mg, 0.038 mmol) and 1-chloro-4-isocyanato-2-(trifluoromethyl)benzene (8.6 mg, 0.038 mmol) were dissolved in THF (0.4 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 1-(4-chloro-3-(trifluoromethyl)phenyl)-3-(4-(2-oxo-2,3-dihydro-1H-thieno[3,4-b][1,4]diazepine-4-yl)phenyl)urea (17 mg, 93%).

¹H NMR (400 MHz, DMSO-d₆) δ 10.46 (1 H, s), 9.25 (1 H, s), 9.19 (1 H, s), 8.13 (1 H, d, J=2.0 Hz), 7.98 (2 H, d, J=8.8 Hz), 7.68-7.60 (4 H, m), 7.47 (1 H, d, J=3.6 Hz), 7.00 (1 H, d, J=3.6 Hz), 3.57 (2 H, s)

(Exact mass 478.05, m/z 479.0538)

Example 40

Synthesis of 1-(4-chlorophenyl)-3-(4-(2-oxo-2,3-dihydro-1H-thieno[3,4-b][1,4]diazepine-4-yl)phenyl)urea

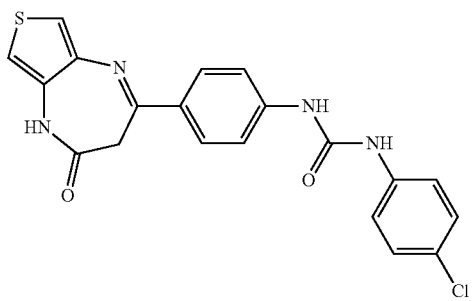 [SMILES: O=C1CC(c2ccc(NC(=O)Nc3ccc(Cl)cc3)cc2)=Nc2cscc2N1]

Then compound F (10 mg, 0.039 mmol) and 1-chloro-4-isocyanatobenzene (7.1 mg, 0.046 mmol) were dissolved in DMF (0.3 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 1-(4-chlorophenyl)-3-(4-(2-oxo-2,3-dihydro-1H-thieno[3,4-b][1,4]diazepine-4-yl)phenyl)urea (8.2 mg, 51%).

¹H NMR (400 MHz, DMSO-d₆) δ10.45 (1 H, s), 9.05 (1 H, s), 8.91 (1 H, s), 7.97 (2 H, d, J=8.8 Hz), 7.59 (2 H, d, J=8.8 Hz), 7.51-7.49 (2 H, m), 7.46 (1 H, d, J=3.6 Hz), 7.35-7.33 (2 H, m), 7.00 (1 H, d, J=3.6 Hz), 3.57 (2 H, s)

(Exact mass 410.06, m/z 411.066)

Example 41

Synthesis of 1-(3-chlorophenyl)-3-(4-(2-oxo-2,3-dihydro-1H-thieno[3,4-b][1,4]diazepine-4-yl)phenyl)urea

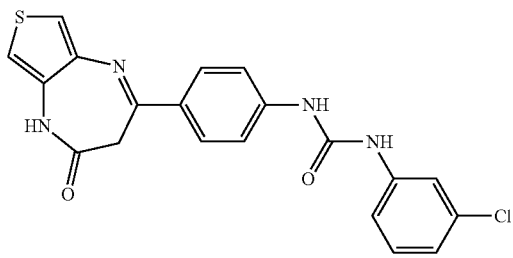 [SMILES: O=C1CC(c2ccc(NC(=O)Nc3cccc(Cl)c3)cc2)=Nc2cscc2N1]

The compound F (10 mg, 0.039 mmol) and 1-chloro-3-isocyanatobenzene (7.1 mg, 0.047 mmol) were dissolved in DMF (0.3 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was crystallized to obtain a target compound 1-(3-chlorophenyl)-3-(4-(2-oxo-2,3-dihydro-1H-thieno[3,4-b][1,4]diazepine-4-yl)phenyl)urea (14 mg, 87%).

¹H NMR (400 MHz, DMSO-d₆) δ10.51 (1 H, s), 10.27 (1 H, s), 10.20 (1 H, s), 7.96 (2 H, d, J=9.2 Hz), 7.70 (1 H, s), 7.60 (2 H, d, J=8.8 Hz), 7.46 (1 H, d, J=3.6 Hz), 7.31-7.30 (2 H, m), 7.02-7.00 (2 H, m), 3.56 (2 H, s)

(Exact mass 410.06, m/z 411.0682)

Example 42

Synthesis of 1-(3,4-dichlorophenyl)-3-(4-(2-oxo-2,3-dihydro-1H-thieno[3,4-b][1,4]diazepine-4-yl)phenyl)urea

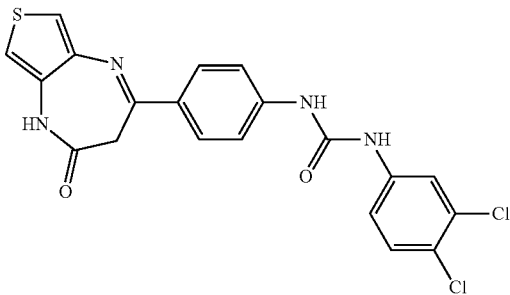 [SMILES: O=C1CC(c2ccc(NC(=O)Nc3ccc(Cl)c(Cl)c3)cc2)=Nc2cscc2N1]

The compound F (8.9 mg, 0.035 mmol) and 1,2-dichloro-4-isocyanatobenzene (7.2 mg, 0.038 mmol) were dissolved in DMF (0.3 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was crystallized to obtain a target compound 1-(3,4-dichlorophenyl)-3-(4-(2-oxo-2,3-dihydro-1H-thieno[3,4-b][1,4]diazepine-4-yl)phenyl)urea (5 mg, 32%).

$^1$H NMR (400 MHz, DMSO-$d_6$) δ 10.45 (1 H, s), 9.16 (1 H, s), 9.09 (1 H, s), 7.98 (2 H, d, J=8.8 Hz), 7.90 (1 H, d, J=2.8 Hz), 7.60 (2 H, d, J=8.8 Hz), 7.53 (1 H, d, J=8.8 Hz), 7.47 (1 H, d, J=4.0 Hz), 7.35 (1 H, dd, J=8.8, 2.4 Hz), 7.00 (1 H, d, J=3.6 Hz), 3.57 (2 H, s)

(Exact mass 444.02, m/z 446.0302)

Example 43

Synthesis of 1-(4-((4-ethylpiperazine-1-yl)methyl)-3-(trifluoromethyl)phenyl)-3-(4-(2-oxo-2,3-dihydro-1H-thieno[3,4-b][1,4]diazepine-4-yl)phenyl)urea

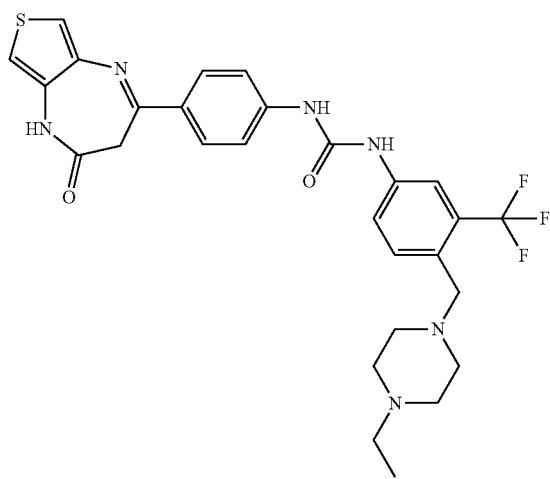 [SMILES: CCN1CCN(Cc2ccc(NC(=O)Nc3ccc(C4=Nc5cscc5NC(=O)C4)cc3)cc2C(F)(F)F)CC1]

The compound F (9.5 mg, 0.038 mmol), 4-nitrophenyl 3-(4-ethylpiperazine-1-yl)-5-(trifluoromethyl)phenylcarbamate (19.3 mg, 0.042 mmol), and TEA (7.7 mg, 0.076 mmol) were dissolved in DMF (0.2 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was crystallized to obtain a target compound 1-(4-((4-ethylpiperazine-1-yl)methyl)-3-(trifluoromethyl)phenyl)-3-(4-(2-oxo-2,3-dihydro-1H-thieno[3,4-b][1,4]diazepine-4-yl)phenyl)urea (5.2 mg, 23%).

$^1$H NMR (400 MHz, DMSO-$d_6$) δ 10.45 (1 H, s), 9.20 (2 H, s), 7.99-7.97 (3 H, m), 7.63-7.59 (4 H, m), 7.47 (1 H, d, J=3.6 Hz), 7.00 (1 H, d, J=3.6 Hz), 3.57 (2 H, s), 3.53 (2 H, s), 2.39-2.28 (10 H, m), 0.98 (3 H, t, J=7.2 Hz)

(Exact mass 570.20, m/z 571.2081)

Example 44

Synthesis of 1-(3,5-dichlorophenyl)-3-(4-(2-oxo-2,3-dihydro-1H-thieno[3,4-b][1,4]diazepine-4-yl)phenyl)urea

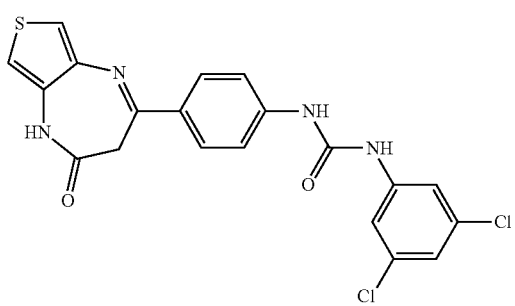 [SMILES: O=C1CC(c2ccc(NC(=O)Nc3cc(Cl)cc(Cl)c3)cc2)=Nc2cscc2N1]

The compound F (10 mg, 0.038 mmol) and 1,3-dichloro-5-isocyanatobenzene (8 mg, 0.043 mmol) were dissolved in DMF (0.2 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was crystallized to obtain a target compound 1-(3,5-dichlorophenyl)-3-(4-(2-oxo-2,3-dihydro-1H-thieno[3,4-b][1,4]diazepine-4-yl)phenyl)urea (14 mg, 80%).

$^1$H NMR (400 MHz, DMSO-$d_6$) δ 10.46 (1 H, s), 9.22 (1 H, s), 9.13 (1 H, s), 7.98 (2 H, d, J=8.8 Hz), 7.60 (2 H, d, J=8.8 Hz), 7.55 (2 H, d, J=2.0 Hz), 7.47 (1 H, d, J=3.6 Hz), 7.19 (1 H, t, J=1.6 Hz), 7.00 (1 H, d, J=4.0 Hz), 3.57 (2 H, s)

(Exact mass 444.02, m/z 446.0299)

Example 45

Synthesis of 1-(2-fluorophenyl)-3-(4-(2-oxo-2,3-dihydro-1H-thieno[3,4-b][1,4]diazepine-4-yl)phenyl)urea

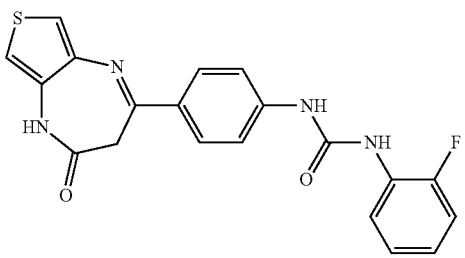 [SMILES: O=C1CC(c2ccc(NC(=O)Nc3ccccc3F)cc2)=Nc2cscc2N1]

The compound F (15 mg, 0.058 mmol) and 1-fluoro-2-isocyanatobenzene (8 mg, 0.058 mmol) were dissolved in THF (6 μl), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 1-(2-fluorophenyl)-3-(4-(2-oxo-2,3-dihydro-1H-thieno[3,4-b][1,4]diazepine-4-yl)phenyl)urea (6 mg, 26%).

$^1$H NMR (400 MHz, DMSO-$d_6$) δ 10.48 (s, 1 H), 9.40 (s, 1 H), 8.65 (d, J=2.5 Hz, 1 H), 8.16 (td, J=8.3, 1.7 Hz, 1 H), 7.99 (d, J=8.9 Hz, 2 H), 7.60 (d, J=8.9 Hz, 2 H), 7.47 (d, J=3.7 Hz, 1 H), 7.25 (ddd, J=11.6, 8.2, 1.4 Hz, 1 H), 7.18-7.13 (m, 1 H), 7.07-6.99 (m, 2 H), 3.57 (s, 2 H).

(Exact mass 394.09, m/z 395.42)

Example 46

Synthesis of 1-(4-chloro-3-(trifluoromethyl)phenyl)-3-(3-(2-oxo-2,3-dihydro-1H-thieno[3,4-b][1,4]diazepine-4-yl)phenyl)urea

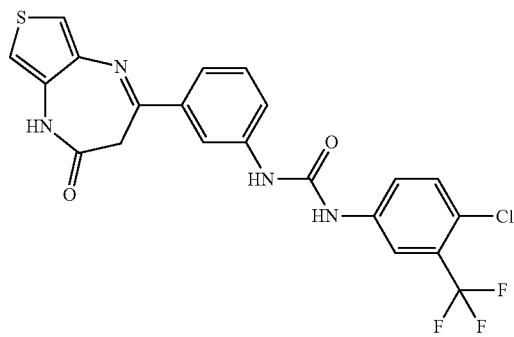 [SMILES: O=C1CC(c2cccc(NC(=O)Nc3ccc(Cl)c(C(F)(F)F)c3)c2)=Nc2cscc2N1]

The compound F (10 mg, 0.038 mmol) and 1-chloro-4-isocyanato-2-(trifluoromethyl)benzene (8.6 mg, 0.038 mmol) were dissolved in DMF (0.2 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was crystallized to obtain a target compound 1-(4-chloro-3-(trifluoromethyl)phenyl)-3-(3-(2-oxo-2,3-dihydro-1H-thieno[3,4-b][1,4]diazepine-4-yl)phenyl)urea (16 mg, 87%).

$^1$H NMR (400 MHz, DMSO-$d_6$) δ10.51 (1 H, s), 9.17 (1 H, s), 9.12 (1 H, s), 8.14 (1 H, t, J=1.8 Hz), 8.12 (1 H, d, J=2.4 Hz), 7.70-7.61 (4 H, s), 7.54 (1 H, d, J=3.6 Hz), 7.44 (1 H, t, J=7.8 Hz), 7.03 (1 H, d, J=3.6 Hz), 3.58 (2 H, s)

(Exact mass 478.05, m/z 479.053)

Example 47

Synthesis of 1-(4-chlorophenyl)-3-(3-(2-oxo-2,3-dihydro-1H-thieno[3,4-b][1,4]diazepine-4-yl)phenyl)urea

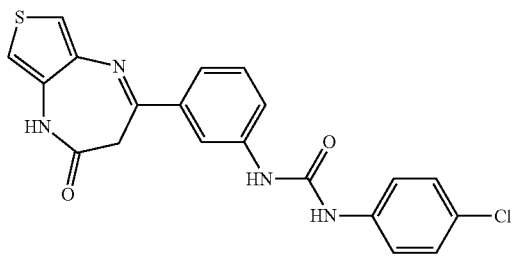 [SMILES: O=C1CC(c2cccc(NC(=O)Nc3ccc(Cl)cc3)c2)=Nc2cscc2N1]

The compound F (10.2 mg, 0.039 mmol), and 1-chloro-4-isocyanatobenzene (7.3 mg, 0.047 mmol) were dissolved in DMF (0.3 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was crystallized to obtain a target compound 1-(4-chlorophenyl)-3-(3-(2-oxo-2,3-dihydro-1H-thieno[3,4-b][1,4] diazepine-4-yl)phenyl)urea (13.2 mg, 82%).

$^1$H NMR (400 MHz, DMSO-$d_6$)δ10.51 (1 H, s), 8.96 (1 H, s), 8.81 (1 H, s), 8.13 (1 H, t, J=1.8 Hz), 7.64-7.61 (2 H, m), 7.53 (1 H, d, J=3.6 Hz), 7.52-7.49 (2 H, m), 7.43 (1 H, t, J=8.0 Hz), 7.35-7.31 (2 H, m), 7.02 (1 H, d, J=4.0), 3.58 (2 H, s)

(Exact mass 410.06, m/z 411.0654)

Example 48

Synthesis of 1-(3-chlorophenyl)-3-(3-(2-oxo-2,3-dihydro-1H-thieno[3,4-b][1,4]diazepine-4-yl)phenyl)urea

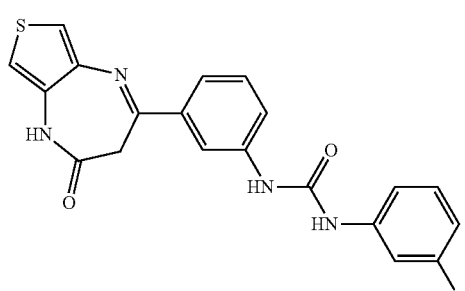

The compound F (10.2 mg, 0.039 mmol) and 1-chloro-3-isocyanatobenzene (7.2 mg, 0.047 mmol) were dissolved in DMF (0.4 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was crystallized to obtain a target compound 1-(3-chlorophenyl)-3-(3-(2-oxo-2,3-dihydro-1H-thieno[3,4-b][1,4] diazepine-4-yl)phenyl)urea (14.3 mg, 89%).

$^1$H NMR (400 MHz, DMSO-$d_6$) δ 10.51 (1 H, s), 9.01 (1 H, s), 8.89 (1 H, s), 8.14 (1 H, t, J=1.6 Hz), 7.73 (1 H, s), 7.62 (2 H, dd, J=7.8, 1.8 Hz), 7.54 (1 H, d, J=3.6 Hz), 7.44 (1 H, t, J=8.0 Hz), 7.31-7.29 (2 H, m), 7.04-7.01 (2 H, m), 3.58 (2 H, s)

(Exact mass 410.06, m/z 411.0651)

Example 49

Synthesis of 1-(4-((4-ethylpiperazine-1-yl)methyl)-3-(trifluoromethyl)phenyl)-3-(3-(2-oxo-2,3-dihydro-1H-thieno[3,4-b][1,4]diazepine-4-yl)phenyl)urea

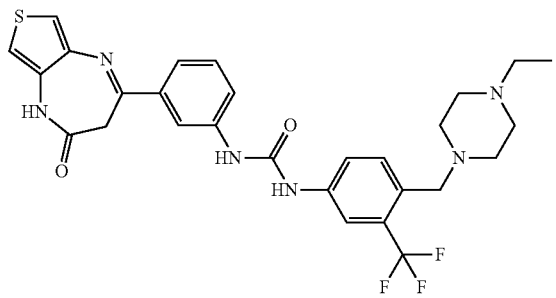 [SMILES: CCN1CCN(Cc2ccc(NC(=O)Nc3cccc(C4=Nc5cscc5NC(=O)C4)c3)cc2C(F)(F)F)CC1]

The compound F (9.5 mg, 0.038 mmol), 4-nitrophenyl 3-(4-ethylpiperazine-1-yl)-5-(trifluoromethyl)phenylcarbamate (19.3 mg, 0.042 mmol) and TEA (7.7 mg, 0.076 mmol) were dissolved in DMF (0.2 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was crystallized to obtain a target compound 1-(4-((4-ethylpiperazine-1-yl)methyl)-3-(trifluoromethyl)phenyl)-3-(3-(2-oxo-2,3-dihydro-1H-thieno[3,4-b][1,4]diazepine-4-yl)phenyl)urea (5.2 mg, 23%).

$^1$H NMR (400 MHz, DMSO-$d_6$)δ10.54 (1 H, s), 9.19 (1 H, s), 9.18 (1 H, s), 8.15 (1 H, t, J=1.6 Hz), 7.93 (1 H, d, J=2.0 Hz), 7.65-7.58 (4 H, m), 7.54 (1 H, d, J=3.6 Hz), 7.43 (1 H, t, J=7.8 Hz), 7.03 (1 H, d, J=3.6 Hz), 3.58 (2 H, s), 3.52 (2 H, s), 2.38-2.28 (10 H, m), 0.98 (3 H, t, J=7.2 Hz) (m/z 571.2061)

Example 50

Synthesis of 1-(3,4-dichlorophenyl)-3-(3-(2-oxo-2,3-dihydro-1H-thieno[3,4-b][1,4]diazepine-4-yl)phenyl)urea

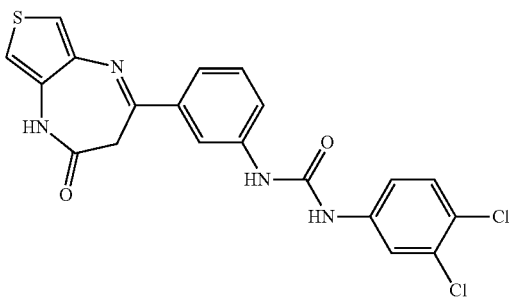 [SMILES: O=C1CC(c2cccc(NC(=O)Nc3ccc(Cl)c(Cl)c3)c2)=Nc2cscc2N1]

The compound F (10 mg, 0.038 mmol) and 1,2-dichloro-4-isocyanatobenzene (10.2 mg, 0.054 mmol) were dissolved in DMF (0.2 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 1-(3,4-dichlorophenyl)-3-(3-(2-oxo-2,3-dihydro-1H-thieno[3,4-b][1,4] diazepine-4-yl)phenyl)urea (15.9 mg, 35%).

$^1$H NMR (400 MHz, DMSO-$d_6$) δ 10.53 (1 H, s), 9.08 (1 H, s), 9.01 (1 H, s), 8.15 (1 H, t, J=2.0 Hz), 7.90 (1 H, t, J=2.4 Hz), 7.64-7.61 (2 H, m), 7.55-7.52 (2 H, s), 7.44 (1 H, t, J=8.0 Hz), 7.35 (1 H, dd, J=8.0, 2.4 Hz), 7.03 (1 H, d, J=3.6 Hz), 3.58 (2 H, s)

(Exact mass 444.02, m/z 446.0292)

Example 51

Synthesis of 1-(3,5-dichlorophenyl)-3-(3-(2-oxo-2,3-dihydro-1H-thieno[3,4-b][1,4]diazepine-4-yl)phenyl)urea

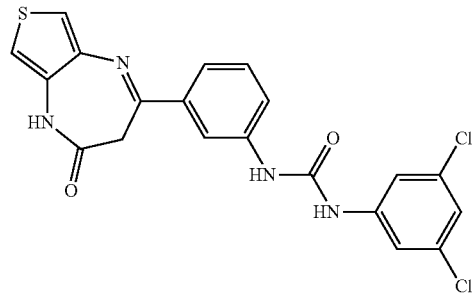 [SMILES: O=C1CC(c2cccc(NC(=O)Nc3cc(Cl)cc(Cl)c3)c2)=Nc2cscc2N1]

The compound F (10 mg, 0.038 mmol) and 1,3-dichloro-5-isocyanatobenzene (10.2 mg, 0.054 mmol) were dissolved in DMF (0.2 ml), and then the solution was stirred at room temperature for 12 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 1-(3,5-dichlorophenyl)-3-(3-(2-oxo-2,3-dihydro-1H-thieno[3,4-b][1,4] diazepine-4-yl)phenyl)urea (12.6 mg, 72%).

$^1$H NMR (400 MHz, DMSO-$d_6$)δ10.53 (1 H, s), 9.16 (1 H, s), 9.07 (1 H, s), 8.15 (1 H, t, J=2.0 Hz), 7.65-7.61 (2 H, m), 7.56-7.54 (3 H, m), 7.44 (1 H, t, J=7.8 Hz), 7.18 (1 H, t, J=1.8 Hz), 7.03 (1 H, d, J=3.6 Hz), 3.58 (2 H, s)

(Exact mass 444.02, m/z 446.029)

Example 52

Synthesis of 1-(2-fluorophenyl)-3-(3-(2-oxo-2,3-dihydro-1H-thieno[3,4-b][1,4]diazepine-4-yl)phenyl)urea

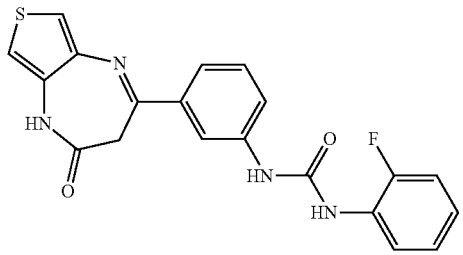 [SMILES: O=C1CC(c2cccc(NC(=O)Nc3ccccc3F)c2)=Nc2cscc2N1]

The compound F (20 mg, 0.077 mmol), and 1-fluoro-2-isocyanatobenzene (10 mg, 0.077 mmol) were dissolved in THF (0.2 ml), and then the solution was stirred at room temperature for 6 hours. After the reaction was completed, ethyl acetate was added and the reaction mixture was washed with a saturated aqueous NaCl solution. The organic layer was dried with sodium sulfate anhydrous and filtered, and then the solvent was removed under reduced pressure. The residue was purified through column chromatography (silica gel, ethyl acetate:Hex=1:1) to obtain a target compound 1-(2-fluorophenyl)-3-(3-(2-oxo-2,3-dihydro-1H-thieno[3,4-b][1,4]diazepine-4-yl)phenyl)urea (30 mg, 98%).

$^1$H NMR (400 MHz, DMSO-$d_6$) δ 10.53 (s, 1 H), 9.33 (s, 1 H), 8.56 (d, J=2.5 Hz, 1 H), 8.19-8.11 (m, 2 H), 7.63 (ddd, J=5.8, 4.8, 1.9 Hz, 2 H), 7.54 (d, J=3.7 Hz, 1 H), 7.44 (t, J=7.9 Hz, 1 H), 7.25 (ddd, J=11.6, 8.2, 1.4 Hz, 1 H), 7.15 (t, J=7.2 Hz, 1 H), 7.05-7.00 (m, 2 H), 3.58 (s, 2 H).

(Exact m/z 394.04, m/z 394.94)

Experimental Example 1

Measurement of Proliferation Inhibition Activity Against A375P Cell Line (Melanoma)

An A375P cell line purchased from ATCC was cultured in a DMEM medium [containing 10% FBS, 1% penicillin/streptomycin] at 37° C. in the presence of 5% $CO_2$. The cultured A375P cell line was taken using 0.05% trypsin-0.02% EDTA, and seeded into a 96-well plate at a density of 5×103 cells per well.

Cell viability was measured using an MTT [3-(4,5-dimethylthiazol-2-yl)-2,5-diphenyltetrazolium bromide] assay (CellTiter 96 Assay, Promega) as follows. 15 µl of dye was placed per well, the cells were cultured for 2 hours, and then treated with 100 µl of a stop solution, and after 24 hours, absorbance was measured. One day after plating, they were treated with compounds. For treatment with compounds, 10 µM of stock was prepared, and serially diluted to one-third in dimethyl sulfoxide (DMSO) to prepare a 12-point test compound plate, and 0.5 µl was added (final concentration DMSO 0.5%). Readings were conducted at a wavelength of 590 nm using EnVision2103, a proliferation inhibition activity value ($GI_{50}$) was calculated using GraphPad Prism 4.0 software, and the results are shown in the following Tables 1 to 3 (maximum potency showed less than 60% of total growth).

In the following Tables 1 to 3, in a case of $GI_{50}$ being 10 to 30 µM, it was indicated as (+), in a case of it being 1 to 10 µM, it was indicated as (++), and in case of being less than 1 µM, it was indicated as (+++).

TABLE 1

| Compound | Substitution | A375P ($GI_{50}$, µM) |
|---|---|---|
| Example 1 | 4-amide | ++ |
| Example 2 | 4-amide | +++ |
| Example 3 | 4-amide | +++ |
| Example 4 | 4-amide | ++ |
| Example 5 | 4-amide | +++ |
| Example 6 | 4-amide | + |
| Example 7 | 4-amide | ++ |
| Example 8 | 4-amide | + |
| Example 9 | 4-amide | + |
| Example 10 | 4-amide | + |
| Example 11 | 4-amide | + |
| Example 12 | 4-amide | + |
| Example 13 | 4-amide | + |
| Example 14 | 4-amide | + |
| Example 15 | 4-amide | + |
| Example 16 | 4-amide | + |
| Example 17 | 4-amide | + |
| Example 18 | 3-amide | ++ |
| Example 19 | 3-amide | + |
| Example 20 | 3-amide | +++ |

TABLE 2

| Compound | Substitution | A375P ($GI_{50}$, µM) |
|---|---|---|
| Example 21 | 3-amide | ++ |
| Example 22 | 3-amide | + |
| Example 23 | 3-amide | + |
| Example 24 | 3-amide | + |
| Example 25 | 3-amide | + |
| Example 26 | 3-amide | + |
| Example 27 | 3-amide | + |
| Example 28 | 3-amide | + |
| Example 29 | 3-amide | + |
| Example 30 | 3-amide | + |
| Example 31 | 3-amide | + |
| Example 32 | 3-amide | + |
| Example 33 | 3-amide | + |
| Example 34 | 3-amide | + |
| Example 35 | 3-amide | + |
| Example 36 | 3-amide | + |
| Example 37 | 3-amide | + |
| Example 38 | 3-amide | + |
| Example 39 | 4-urea | +++ |
| Example 40 | 4-urea | ++ |

TABLE 3

| compound | Substitution | A375P ($GI_{50}$, µM) |
|---|---|---|
| Example 41 | 4-urea | + |
| Example 42 | 4-urea | ++ |

TABLE 3-continued

| compound | Substitution | A375P (GI$_{50}$, μM) |
|---|---|---|
| Example 43 | 4-urea | +++ |
| Example 44 | 4-urea | +++ |
| Example 45 | 4-urea | + |
| Example 46 | 3-urea | ++ |
| Example 47 | 3-urea | ++ |
| Example 48 | 3-urea | +++ |
| Example 49 | 3-urea | +++ |
| Example 50 | 3-urea | ++ |
| Example 51 | 3-urea | + |
| Example 52 | 3-urea | + |

Referring to Tables 1 to 3, it appears that in the compounds of the examples, the tail groups of $R^a$ have an important influence on the activities, which shows that the activities of the compounds of the examples are more sensitive to a secondary hydrophobic pocket.

Among the compounds of the examples, particularly, the compounds of Examples 2, 3, 5, 20, 39, 43, 44, 48, and 49, they showed significant effects against A375P. Among them, the compound of Example 43 showed a GI$_{50}$ value against A375P of 1.45 μM, and thus exhibited better efficacy than Sorafenib (2.74 μM).

Experimental Example 2

Evaluation of Activities on Various Kinases

Using the compound of Example 43 (1-(4-(4-((4-ethylpiperazine-1-yl)methyl)-3-(trifluoromethyl)phenyl)-3-(4-(2-oxo-2,3-dihydro-1H-thieno[3,4-b][1,4]diazepine-4-yl)phenyl)urea), kinase panel screening was conducted against 35 kinds of kinases at a concentration of 10 μM, and the results are shown in the following Tables 4 and 5 (percentages of enzymatic inhibitions exerted by compound 43 (10 μM) on 30 selected protein kinases).

Further, the IC$_{50}$ values (50% inhibition concentration) of the compound of Example 43 against various kinases were calculated using GraphPad Prism 4.0 software, and the results are shown in the following Table 6.

TABLE 4

| Kinase | % Inhibition |
|---|---|
| AKT1 | 3.23 |
| ALK | 41.0 |
| Aurora A | 20.4 |
| BRAF | 32.0 |
| BRAF (V599E) | 43.9 |
| c-Kit | 85.9 |
| c-MET | 21.7 |
| c-Src | 55.2 |
| CDK1/cyclin B | 2.68 |
| CDK2/cyclin E | 0.28 |
| EGFR | 24.8 |
| ERK1 | 1.22 |
| FAK/PTK2 | 41.2 |
| FGFR2 | 29.9 |
| FGFR3 | 45.0 |
| FLT3 | 98.9 |
| FMS | 100 |
| GSK3b | 8.62 |
| IGF1R | 1.34 |
| KDR/VEGFR2 | 60.2 |

TABLE 5

| Kinase | % Inhibition |
|---|---|
| LCK | 79.3 |
| LYN | 89.4 |
| MEK1 | 5.26 |
| P38a/MAPK14 | 89.9 |
| RAF1 | 86.2 |
| ROS/ROS1 | 3.71 |
| SYK | 57.4 |
| FGFR1 | 34.4 |
| FLT1/VEGFR1 | 79.1 |
| FLT4/VEGFR3 | 95.8 |
| ITK | 20.7 |
| PDGFRa | 85.9 |
| PDGFRb | 96.1 |
| RET | 99.1 |
| TIE2/TEK | 64.9 |
| / | / |

TABLE 6

| Kinase | IC$_{50}$ (μM) | Kinase | % Inhibition |
|---|---|---|---|
| c-Kit | 8.73E-07 | FLT4/VEGFR3 | 7.35E-07 |
| FLT3 | 2.79E-08 | PDGFRa | 3.68E-07 |
| FMS | 3.73E-09 | PDGFRb | 6.34E-08 |
| LYN | 1.18E-06 | RET | 7.16E-08 |
| RAF1 | 5.32E-07 | / | / |

Referring to Tables 4 to 6, it was confirmed that, particularly, the compound of Example 43 has strong anticancer activity.

The invention claimed is:

1. A compound represented by the following Chemical Formula 1 or a pharmaceutically acceptable salt thereof:

[Chemical Formula 1]

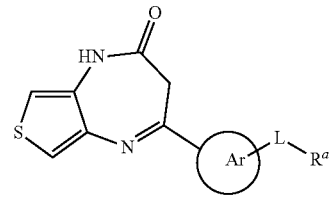

in Chemical Formula 1,

Ar is C6-20 arylene or heteroarylene, wherein the heteroarylene is a divalent group derived from one aromatic compound selected from the group consisting of pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, pyridine, pyridazine, pyrimidine, pyrazine, 1,3,5-triazine, 1,2,4-triazine, 1,2,3-triazine, 1,2,4,5-tetrazine, 1,2,3,4-tetrazine, and 1,2,3,5-tetrazine, carbazole, indole, isoindole, indolizine, indazole, benzimidazole, benzotriazole, purine, naphthimidazole, phenanthrimidazole, pyridimidazole, pyrazineimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3-b]thiophene, thieno[3,2-b]thiophene, dithienothiophene, dithienopyridine, isobenzothiophene, dibenzothiophene, and benzothiadiazothiophene;

L is $-NR^1-C(=O)-$, $-C(=O)-NR^1-$, $-C(=O)-NR^1-C(=O)-$, $-NR^1-C(=O)-NR^2-$, or $-NR^1-C(=O)-NR^2-C(=O)-$;

$R^1$ and $R^2$ are each independently hydrogen, a C1-5 alkyl, a C2-6 unsaturated alkyl, or a C1-5 alkylamine;

$R^a$ is 3-chloro-4-(trifluoromethyl)phenyl, 4-chloro-4-(trifluoromethyl)phenyl, 3-(trifluoromethyl)phenyl, 3-(4-methyl-1H-imidazole-1-yl)-5-(trifluoromethyl)phenyl, 3-(morpholin-4-yl)-5-(trifluoromethyl)phenyl, 4-(morpholin-4-yl)-3-(trifluoromethyl)phenyl, 3-(morpholin-4-yl)-4-(trifluoromethyl)phenyl, 3-(morpholin-3-yl)-5-(trifluoromethyl)phenyl, biphenyl-4-yl, biphenyl-2-yl, 1-phenyl-5-(trifluoromethyl)-pyrazole-4-yl, 1-acetylpiperidin-4-yl, bis(4-chlorophenyl)methyl, 2-chloro-5-(4-chlorobenzyl)phenyl, pyridinyl, pyrazinyl, 6-fluorophenyl-methyl, 3-(4-methylpiperazine-1-yl)-5-(trifluoromethyl)phenyl), 3-(4-hydroxylpiperazine-1-yl)-5-(trifluoromethyl)phenyl, 4-(4-ethylpiperazine-1-yl)-3-(trifluoromethyl)phenyl, 4-((4-ethylpiperazine-1-yl)methyl)-3-(trifluoromethyl)phenyl, 4-(1-methylpiperazine-4-yloxy)-3-(trifluoromethyl)phenyl, chlorophenyl, 1H-indol-3-yl-methyl, 2-[(2-cyanophenyl)sulfanyl]phenyl, quinolinyl, biphenyl-4-yl-methyl, 2,4-dimethylphenyl, 6-hydroxy-2,5,7,8-tetramethyl-3,4-dihydro-2H-chromen-2-yl, 2,3-dichlorophenyl, 4-[(4-ethylpiperazine-1-yl)methyl]-3-(trifluoromethyl)phenyl, fluorophenyl, 1H-benzotriazol-5-yl, 5-(4-methoxyphenyl)furan-2-yl, dihydro-1H-indol-2-yl, 3,4-di-methoxyphenyl)methyl, naphthyl, benzothienyl, pyranyl, isoxazolyl, pyrazolyl, pyridazinyl, thiazolyl, thienyl, pyrimidinyl, imidazolyl, pyrolyl, dihydropyrolyl, oxazolyl, triazolyl, thidiazolyl, benzimidazolyl, quinolyl, tetrahydroquinolyl, benzothiazolyl, benzothiazophenyl, benzodioxolyl, indolyl, or dihydrobenzofuranyl.

2. The compound or a pharmaceutically acceptable salt thereof according to claim 1,
wherein the compound represented by Chemical Formula 1 is one or more compounds selected from the group consisting of the following compounds:

4-chloro-N-(4-(2-oxo-2,3-dihydro-1H-thieno[3,4-b][1,4]diazepin-4-yl)phenyl)-3-(trifluoromethyl)benzamide;
3-(4-methyl-1H-imidazol-1-yl)-N-(4-(2-oxo-2,3-dihydro-1H-thieno[3,4-b][1,4]diazepine-4-yl)phenyl)-5-(trifluoromethyl)benzamide;
3-morpholino-N-(4-(2-oxo-2,3-dihydro-1H-thieno[3,4-b][1,4]diazepine-4-yl)phenyl)-5-(trifluoromethyl)benzamide;
4-morpholino-N-(4-(2-oxo-2,3-dihydro-1H-thieno[3,4-b][1,4]diazepine-4-yl)phenyl)-3-(trifluoromethyl)benzamide;
N-(4-(2-oxo-2,3-dihydro-1H-thieno[3,4-b][1,4]diazepine-4-yl)phenyl)biphenyl-4-carboxamide;
N-(4-(2-oxo-2,3-dihydro-1H-thieno[3,4-b][1,4]diazepine-4-yl)phenyl)biphenyl-2-carboxamide;
N-(4-(2-oxo-2,3-dihydro-1H-thieno[3,4-b][1,4]diazepine-4-yl)phenyl)-1-phenyl-5-(trifluoromethyl)-1H-pyrazole-4-carboxamide;
1-acetyl-N-(4-(2-oxo-2,3-dihydro-1H-thieno[3,4-b][1,4]diazepin-4-yl)phenyl)piperidine-4-carboxamide;
2,2-bis(4-chlorophenyl)-N-(4-(2-oxo-2,3-dihydro-1H-thieno[3,4-b][1,4]diazepine -4-yl)phenyl)acetamide;
N-(4-(2-oxo-2,3-dihydro-1H-thieno[3,4-b][1,4]diazepine-4-yl)phenyl)isonicotinamide;
N-(4-(2-oxo-2,3-dihydro-1H-thieno[3,4-b][1,4]diazepine-4-yl)phenyl)pyrazine-2-carboxamide;
3-(4-methylpiperazine-1-yl)-N-(4-(2-oxo-2,3-dihydro-1H-thieno[3,4-b][1,4]diazepine-4-yl)phenyl)-5-(trifluoromethyl)benzamide;
4-chloro-N-(4-(2-oxo-2,3-dihydro-1H-thieno[3,4-b][1,4]diazepin-4-yl)phenyl)benzamide;
2-(1H-indol-3-yl)-N-(4-(2-oxo-2,3-dihydro-1H-thieno[3,4-b][1,4]diazepine-4-yl)phenyl)acetamide;
2-(2-cyanophenylthio)-N-(4-(2-oxo-2,3-dihydro-1H-thieno[3,4-b][1,4]diazepine-4-yl)phenyl)benzamide;
2-(biphenyl-4-yl)-N-(4-(2-oxo-2,3-dihydro-1H-thieno[3,4-b][1,4]diazepine-4-yl)phenyl)acetamide;
3,5-dimethyl-N-(4-(2-oxo-2,3-dihydro-1H-thieno[3,4-b][1,4]diazepine-4-yl)phenyl)benzamide;
4-chloro-N-(3-(2-oxo-2,3-dihydro-1H-thieno[3,4-b][1,4]diazepine-4-yl)phenyl)-3-(trifluoromethyl)benzamide;
3-(4-methyl-1H-imidazol-1-yl)-N-(3-(2-oxo-2,3-dihydro-1H-thieno[3,4-b][1,4]diazepine-4-yl)phenyl)-5-(trifluoromethyl)benzamide;
3-morpholino-N-(3-(2-oxo-2,3-dihydro-1H-thieno[3,4b][1,4]diazepine-4-yl)phenyl)-5-(trifluoromethyl)benzamide;
4-morpholino-N-(3-(2-oxo-2,3-dihydro-1H-thieno[3,4-b][1,4]diazepine-4-yl)phenyl)-3-(trifluoromethyl)benzamide;
N-(3-(2-oxo-2,3-dihydro-1H-thieno[3,4-b][1,4]diazepine-4-yl)phenyl)biphenyl-4-carboxamide;
N-(3-(2-oxo-2,3-dihydro-1H-thieno[3,4-b][1,4]diazepine-4-yl)phenyl)biphenyl-2-carboxamide;
N-(3-(2-oxo-2,3-dihydro-1H-thieno[3,4-b][1,4]diazepine-4-yl)phenyl)-1-phenyl-5-(trifluoromethyl)-1H-pyrazole-4-carboxamide;
1-acetyl-N-(3-(2-oxo-2,3-dihydro-1H-thieno[3,4-b][1,4]diazepin-4-yl)phenyl)piperidine-4-carboxamide;
2,2-bis(4-chlorophenyl)-N-(3-(2-oxo-2,3-dihydro-1H-thieno[3,4-b][1,4]diazepine -4-yl)phenyl)acetamide;
N-(3-(2-oxo-2,3-dihydro-1H-thieno[3,4-b][1,4]diazepine-4-yl)phenyl)isonicotinamide;
N-(3-(2-oxo-2,3-dihydro-1H-thieno[3,4-b][1,4]diazepine-4-yl)phenyl)pyrazine-2-carboxamide;
3-(4-methylpiperazine-1-yl)-N-(3-(2-oxo-2,3-dihydro-1H-thieno[3,4-b][1,4]diazepine-4-yl)phenyl)-5-(trifluoromethyl)benzamide;
4-chloro-N-(3-(2-oxo-2,3-dihydro-1H-thieno[3,4-b][1,4]diazepine-4-yl)phenyl)benzamide;
2-(1H-indol-3-yl)-N-(3-(2-oxo-2,3-dihydro-1H-thieno[3,4-b][1,4]diazepine-4-yl)phenyl)acetamide;
2-(2-cyanophenylthio)-N-(3-(2-oxo-2,3-dihydro-1H-thieno[3,4-b][1,4]diazepine-4-yl)phenyl)benzamide;
2-(biphenyl-4-yl)-N-(3-(2-oxo-2,3-dihydro-1H-thieno[3,4-b][1,4]diazepine-4-yl)phenyl)acetamide;
3,5-dimethyl-N-(3-(2-oxo-2,3-dihydro-1H-thieno[3,4-b][1,4]diazepine-4-yl)phenyl)benzamide;
2-(2-fluorophenyl)-N-(3-(2-oxo-2,3-dihydro-1H-thieno[3,4-b][1,4]diazepine-4-yl)phenyl)acetamide;
N-(3-(2-oxo-2,3-dihydro-1H-thieno[3,4-b][1,4]diazepine-4-yl)phenyl)quinoline-2-carboxamide;
N-(3-(2-oxo-2,3-dihydro-1H-thieno[3,4-b][1,4]diazepin-4-yl)phenyl)quinoline-3-carboxamide;
(R)-6-hydroxy-2,5,7,8-tetramethyl-N-(3-(2-oxo-2,3-dihydro-1H-thieno[3,4-b][1,4]diazepine-4-yl)phenyl)chroman-2-carboxamide;

1-(4-chloro-3-(trifluoromethyl)phenyl)-3-(4-(2-oxo-2,3-dihydro-1H-thieno[3,4-b][1,4]diazepine-4-yl)phenyl)urea;

1-(4-chlorophenyl)-3-(4-(2-oxo-2,3-dihydro-1H-thieno[3,4-b][1,4]diazepine-4-yl)phenyl)urea;

1-(3-chlorophenyl)-3-(4-(2-oxo-2,3-dihydro-1H-thieno[3,4-b][1,4]diazepine-4-yl)phenyl)urea;

1-(3,4-dichlorophenyl)-3-(4-(2-oxo-2,3-dihydro-1H-thieno[3,4-b][1,4]diazepine-4-yl)phenyl)urea;

1-(4-((4-ethylpiperazine-1-yl)methyl)-3-(trifluoromethyl)phenyl)-3-(4-(2-oxo-2,3-dihydro-1H-thieno[3,4-b][1,4]diazepine-4-yl)phenyl)urea;

1-(3,5-dichlorophenyl)-3-(4-(2-oxo-2,3-dihydro-1H-thieno[3,4-b][1,4]diazepine-4-yl)phenyl)urea;

1-(2-fluorophenyl)-3-(4-(2-oxo-2,3-dihydro-1H-thieno[3,4-b][1,4]diazepine-4-yl)phenyl)urea;

1-(4-chloro-3-(trifluoromethyl)phenyl)-3-(3-(2-oxo-2,3-dihydro-1H-thieno[3,4-b][1,4]diazepine-4-yl)phenyl)urea;

1-(4-chlorophenyl)-3-(3-(2-oxo-2,3-dihydro-1H-thieno[3,4-b][1,4]diazepine-4-yl)phenyl)urea;

1-(3-chlorophenyl)-3-(3-(2-oxo-2,3-dihydro-1H-thieno[3,4-b][1,4]diazepine-4-yl)phenyl)urea;

1-(4-((4-ethylpiperazine-1-yl)methyl)-3-(trifluoromethyl)phenyl)-3-(3-(2-oxo-2,3-dihydro-1H-thieno[3,4-b][1,4]diazepine-4-yl)phenyl)urea;

1-(3,4-dichlorophenyl)-3-(3-(2-oxo-2,3-dihydro-1H-thieno[3,4-b][1,4]diazepine-4-yl)phenyl)urea;

1-(3,5-dichlorophenyl)-3-(3-(2-oxo-2,3-dihydro-1H-thieno[3,4-b][1,4]diazepine-4-yl)phenyl)urea; and 1-(2-fluorophenyl)-3-(3-(2-oxo-2,3-dihydro-1H-thieno[3,4-b][1,4]diazepine-4-yl)phenyl)urea.

3. A pharmaceutical composition comprising an effective amount of a compound represented by Chemical Formula 1 according to claim 1 and a pharmaceutically acceptable carrier.

\* \* \* \* \*